United States Patent [19]
Gallant et al.

[11] Patent Number: 5,305,202
[45] Date of Patent: Apr. 19, 1994

[54] AMBULATORY ECG ANALYSIS SYSTEM

[75] Inventors: Stuart L. Gallant, Owings Mills; Paul R. Caron, Laurel; Walter E. Palmer, Catonsville, all of Md.; David J. Lubocki, Bellevue, Wash.

[73] Assignee: Quinton Instrument Company, Seattle, Wash.

[21] Appl. No.: 790,045

[22] Filed: Nov. 12, 1991

[51] Int. Cl.$^5$ ............................................. G06F 15/00
[52] U.S. Cl. .............................. 364/413.06; 364/487; 128/696
[58] Field of Search ..................... 364/413.06, 487; 128/695, 696; 395/924

[56] References Cited

U.S. PATENT DOCUMENTS

| | | | |
|---|---|---|---|
| Re. 29,921 | 2/1979 | Cherry et al. | 364/900 |
| 3,267,933 | 8/1966 | Mills et al. | 128/2.06 |
| 3,672,353 | 6/1972 | Crovella et al. | 128/2.06 |
| 3,779,237 | 12/1973 | Goeltz et al. | 128/2.06 |
| 3,822,696 | 7/1974 | Ekstrom et al. | 128/2.06 |
| 3,824,990 | 7/1974 | Baule | 128/2.06 |
| 3,832,994 | 9/1974 | Bicher et al. | 128/2.06 |
| 3,853,119 | 12/1974 | Peterson et al. | 128/2.06 |
| 3,858,034 | 12/1974 | Anderson | 235/151.3 |
| 3,874,370 | 4/1975 | Harris et al. | 128/2.06 |
| 3,880,147 | 4/1975 | Gruenke et al. | 128/2.06 |
| 3,913,567 | 10/1975 | Streckmann | 128/2.06 |
| 3,940,692 | 2/1976 | Neilson | 324/77 |
| 4,006,737 | 2/1977 | Cherry | 128/2.06 |
| 4,023,564 | 5/1977 | Valiquette et al. | 128/2.06 |
| 4,098,267 | 7/1978 | Stein et al. | 128/2.06 |
| 4,211,238 | 7/1980 | Shu et al. | 128/700 |
| 4,316,249 | 2/1982 | Gallant et al. | 364/413.06 |
| 4,333,475 | 6/1982 | Moreno et al. | 128/711 |
| 4,336,810 | 6/1982 | Anderson et al. | 128/702 |
| 4,339,800 | 7/1982 | Woods | 364/417 |
| 4,417,306 | 11/1983 | Citron et al. | 364/415 |
| 4,422,081 | 12/1983 | Woods | 346/33 |
| 4,467,324 | 8/1984 | Bachman | 340/722 |
| 4,476,874 | 10/1984 | Taenzer et al. | 128/663 |
| 4,493,325 | 1/1985 | Hartlaub et al. | 128/419 PG |
| 4,499,904 | 2/1985 | Sidorenko et al. | 128/703 |
| 4,532,934 | 8/1985 | Kelen | 128/697 |
| 4,577,639 | 3/1986 | Simon et al. | 128/709 |
| 4,624,263 | 11/1986 | Slavin | 128/710 |
| 4,680,708 | 7/1987 | Ambos et al. | 364/417 |

(List continued on next page.)

OTHER PUBLICATIONS

SpaceLabs, "Windows To The Heart", 1990.
Author unknown, "Delta Scan Holter System & Scanning Service", date unknown, p. 28.
Author unknown, "Experts Say Surgery Can Prevent Strokes", date unknown, p. 17.

(List continued on next page.)

Primary Examiner—Roy N. Envall, Jr.
Assistant Examiner—Laura Brutman
Attorney, Agent, or Firm—Andrew J. Beck; Montgomery W. Smith; Gene B. Kartchner

[57] ABSTRACT

An ECG analysis system for use in conjunction with an ambulatory ECG recorder. The invention includes a playback deck which is capable of receiving and downloading information from a cassette tape to a dedicated digital analysis unit. The playback deck is capable of receiving information from the cassette tape during rewind of the tape therein as well as during playback of the tape. The dedicated digital analysis unit includes a superimposition template and a minute-by-minute ECG template which allow interaction between the dedicated digital analysis unit and the operator for simplification of analysis, manipulation, editing, and report generation. The system is capable of processing information from a cassette tape while it is being rewound in the playback deck and producing preliminary summary report information related to ECG data on the tape for use by a system operator before the tape completes its rewind operation. The playback deck also includes separate analog and digital circuit boards for isolating digital analysis operations from analog data manipulation operations and a speed control system for monitoring and correcting playback speeds of the tape in the playback deck.

23 Claims, 6 Drawing Sheets

U.S. PATENT DOCUMENTS

| | | | |
|---|---|---|---|
| 4,883,065 | 11/1989 | Kelen | 128/711 |
| 4,896,677 | 1/1990 | Kaneko et al. | 128/696 |
| 4,938,228 | 7/1990 | Richter et al. | 128/690 |
| 4,958,641 | 9/1990 | Digby et al. | 128/702 |
| 5,224,486 | 7/1993 | Lerman et al. | 128/696 |
| 5,238,001 | 8/1993 | Gallant et al. | 128/700 |

OTHER PUBLICATIONS

Medical Electronics, "Holter Monitoring", date unknown, pp. 92, 94, 96.

Loring et al., "Contemporary Ambulatory ECG Recording: Current Trends and Controversies", date unknown, five pages.

Biomedical Technology Information Service, "Routine Holter Monitoring for Myocardial Ischemia", May 1, 1991, pp. 1 and 87.

Quinton Instrument Co., "Tape-Based Holter Screeners with Immediate Reports", Apr. 1991, six pages.

Oxford, "New Medilog 4500", date unknown, two pages.

Fukuda, "Ambulatory ECG Analysis System", date unknown, four pages.

Quinton Instrument Co., "Immediate, Tape-Based Holter Reports", Jul. 1990.

Knoebel et al., "Guidelines for Ambulatory Electrocardiography", Jan. 1989, pp. 206–215.

ECRI, "Health Devices", Aug, 17, 1989, pp. 295–321.

Medical Electronics, "Pacemakers", date unknown, pp. 91–92.

Benhorin et al., "A Directory of Ambulatory ECG Monitoring Equipment", date unknown, pp. 15–25.

Abrash, "EGA and VGA Animation", 1989, pp. 18–26.

Sheffield et al., "Recommendations for Standards of Instrumentation and Practice in the Use of Ambulatory Electrocardiography", Mar. 1985, pp. 626A–636A.

Quinton Instrument Co., "Immediate Reports form a Tape-Based Holter System", Apr. 1991.

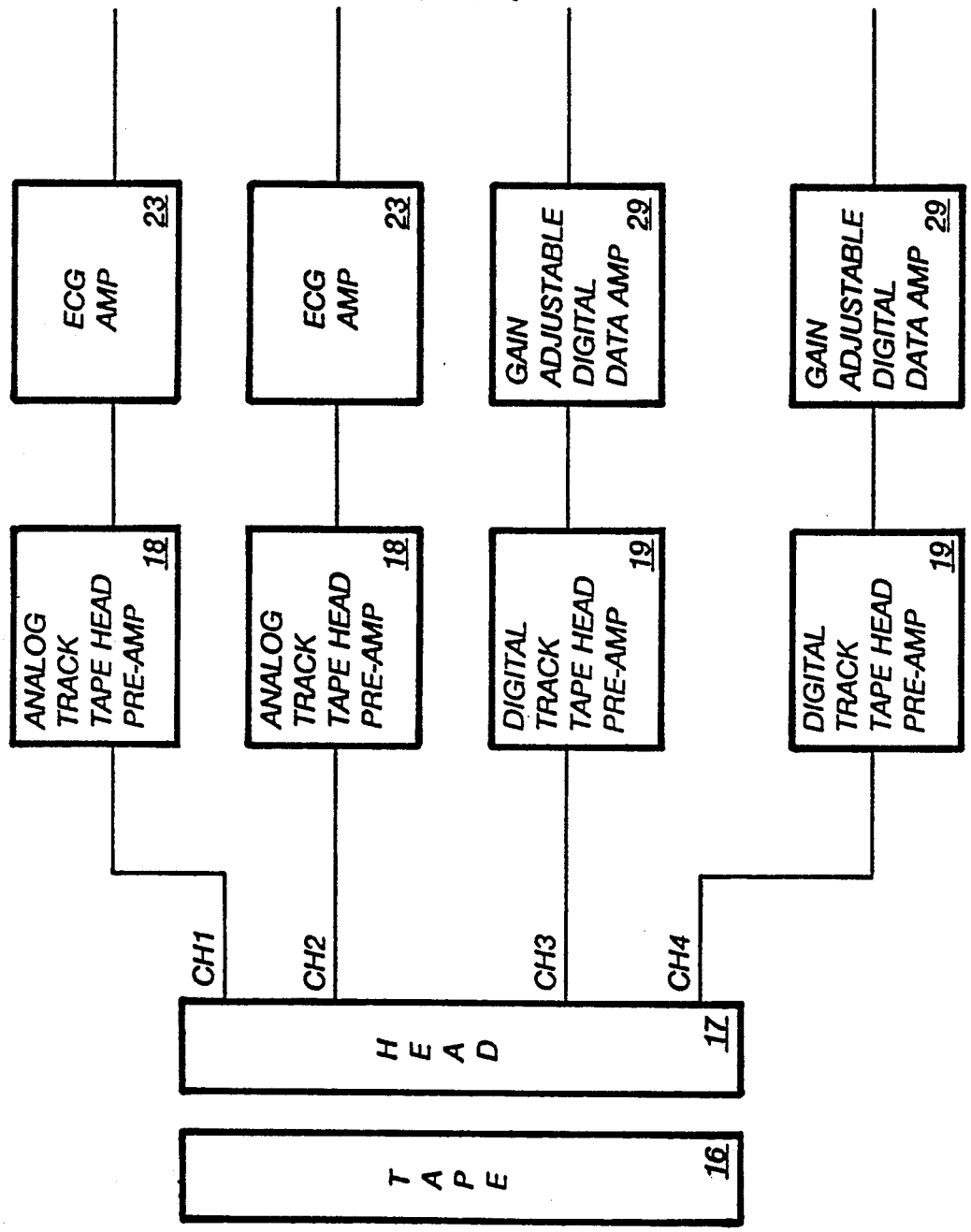

AMBULATORY ECG ANALYSIS SYSTEM

BACKGROUND OF THE INVENTION

1. Field of the Invention

The invention relates generally to electrocardiography systems. More specifically, the invention relates to an ambulatory ECG analysis system for manipulating and analysis of analog and digital ECG data.

2. Prior Art

ECG analysis systems are used to record and analyze characteristics of the electrical signals generated by a patient's heart, often over an extended period of time. Analysis over an extended period is usually performed in conjunction with a recorder which collects information from the patient related to the patient's ECG over a predetermined period, and stores the information for later evaluation. An analyzer, often referred to as a "scanner", is then used to analyze the collected information. Scanners usually include a playback deck for downloading information from a cassette tape obtained from the recorder, and a processing unit such as a computer, for analyzing the data and recording and editing the results. The scanner may also include a monitor for allowing the physician to display data for review, and/or a printer for allowing hard copies of data and analysis reports to be made.

It has become increasingly important for scanners to be automated in order to limit the time in which it takes to process, analyze, and report data to the physician. Further, it has become increasingly important to increase the accuracy of the data collected and the data analysis methods in order to allow more thorough diagnosis to be performed.

Prior art ECG recorders are generally designed for portable, long term detection of ECG signals from a patient over an extended monitoring period. The recordings made are subsequently used to detect abnormalities in the heart's electro activity caused by routine daily activity, or heightened emotional or physical states. The recordings are studied and reviewed to form diagnoses, such as the efficacy of drug therapy treatments or heart pacemaker performance.

ECG analyses have historically been performed in three different ways: 1) Technician analysis; 2) Retrospective analysis; and 3) Real-time analysis.

Technician analysis requires a highly skilled person to perform a visual and audio review of the ECG data as it is displayed on a monitor at high speeds. The monitor superimposes the ECG wave forms on top of each other at a very rapid pace, such as 120 times faster than real-time, with a audio signal being produced in conjunction with each beat. The technicians analysis includes detection of variations in sound and position of abnormal signals from the more common sound and position pattern of the majority of "normal" heart beats. The technician then saves and prints representative strips of ECG data which includes the abnormal ECG wave forms. The technician also often writes a summary document for the entire monitoring period which outlines the particularly noted abnormal ECG events.

Retrospective analysis of ECG data only occurs after the completion of the entire heart monitoring period. Commonly, the ECG data has been previously collected on a recording medium such as a cassette or reel to reel tape and downloaded into the analysis system at a very high speed, such as 60 to 240 times faster than real-time. In retrospective analysis, the analog ECG data taken from the tape is converted into digital format before analysis, editing, and reporting of the collected digital data is performed. During analysis, the technician is often allowed to define the parameters used to detect beat abnormalities if desired.

Although retrospective analysis offers significant time savings to a physician or technician over technician analysis, there are still significant time and position interface requirements involved in the use of retrospective analysis. Typically, to make use of the entire body of data collected on the tape, the entire tape must be converted into digital format and downloaded into the retrospective analysis system. This requires at least one pass of the entire tape, and often a second entire pass before analysis, editing and report records can be generated. Then, after analysis is complete, the digital signals must be converted back to analog for graphic printout of the ECG wave forms. The analysis process can therefore consume a full hour of the physician's time before a final report of a complete monitoring period can be generated.

Further, the accuracy of reports generated through retrospective analysis are very much dependent on the physician's or technician's knowledge of ECG analysis systems and his or her ability to correctly set parameters for abnormal ECG waveforms, and for arrhythmia and ST segment level detection and measurement, and so forth. Even though the analyses themselves may be automated or manually carried out, the results are nevertheless considered to be relatively subjective.

Real-time analysis (RTA) includes the use of a processor and solid state memory to keep pace with the ECG data as it is collected by the recorder during the monitoring period. At the completion of a monitoring period, the data is transferred to a real-time analysis system where it is processed to allow storage, retrieval and report generation. Further, in some real-time analysis systems, a limited amount of editing is also possible. Physician and technician time involved in real-time analysis is very minimal.

A major drawback with real-time analysis systems is that the recorder is generally limited in the amount of data it can store during the monitoring period. It has therefore been necessary for prior art recorders to be designed to either "compress" the monitoring period data into its solid state memory, or to "selectively store" only abnormal ECG data. In the first case, "compressed" data often results in significant shape distortion of the ECG signals and only allows "abbreviated" ECG signals to be retrieved. When the complete ECG data is later printed by the real-time analysis system, gaps will appear between samples of ECG data, thus reducing the accuracy of the report, and distorting the shape of the ECG waveforms.

Alternatively, the recorder may be designed to "selectively store" only abnormal ECG data in order to avoid the necessity of compression. However, full disclosure (FD) capability is subsequently lost, or shown only in analysis as trends, graphs, histograms, and numerical summaries, all being limited to statistical data which cannot be verified.

There therefor exists a need in the art to develop a real-time analysis system which continuously performs digital real-time analysis of ECG signals while simultaneously continuously records the ECG signals in analog format on tape for future full disclosure. There further exists a need in the art to develop a system including tape recording of analog ECG data which allows rapid full disclosure summary report generation with minimum physician/technician interface.

OBJECTS AND SUMMARY OF THE INVENTION

An object of the present invention is to provide and ECG analysis system which can perform real-time analysis on ECG data received from a patient.

Another object of the present invention to provide an ECG analysis system which can accept ECG signals recorded in analog mode, along with analysis information recorded in digital mode.

It is another object of the present invention to provide a real-time analysis system which is capable of regenerating and reporting summary data collected over an entire monitoring period, without the necessity of downloading the complete ECG data and analysis information from the recording medium into the system.

It is further an object of the present invention to provide a real-time analysis system which is capable of receiving data from a tape medium corresponding to monitoring period summary information while the tape medium is being rewound in the system.

Another object of the present invention is to provide a real-time analysis system which allows for real-time annotation and subsequent display of heart beat morphologies to each ECG waveform, including normal, abnormal or paced beat morphologies.

These and other objects of the present invention are realized in a first preferred embodiment of a real-time analysis system including; a data analysis unit which may be in the form of a complete personal computer (PC) unit including a keyboard; a playback deck interconnected with the data analysis unit by an interface cable; and a printer. The analysis system of the present invention may also include a display monitor for graphic representation of summary information and superimposition viewing of ECG wave forms, and for simplifying editing and report preparation. Further, an ECG monitor system according to the present invention may include an ECG recorder such as that described in co-pending U.S. patent application Ser. No. 07/790,035 entitled RECORDER UNIT FOR AMBULATORY ECG MONITORING SYSTEM, filed Nov. 12, 1991, which is incorporated herein by reference (and referred to hereinafter as the "the above-identified co-pending application").

The analysis system of the present invention is capable of downloading data from a tape recorded on prior art-type ECG recorder units in which ECG signals are recorded in analog form on one or a plurality of data tracks on a cassette tape. More importantly however, the present invention is capable of downloading data recorded on the ECG recorder unit as described in the above-identified co-pending application, to generate a complete arrhythmia analysis.

Initially, the ECG recorder of the above-identified copending application detects and processes the R-wave of each ECG complex to perform an initial arrhythmia analysis which includes heart beat morphology classifications, including normal (N), abnormal(V), and paced (P) beats. The post processing phase carried out by the analysis system of the present invention includes a final arrythmia analysis including rhythm patterns and storage of sample ECG rhythm strips to give essentially a dual pass analysis of the recorded information, providing enhanced accuracy and speed as well as increased ability to detect and classify heart beat patterns. If desired, the analysis system can display minute-by-minute ECG data analysis information including an annotated and color coded analog display of each ECG complex. Also, if desired, the monitor may be used by the analysis system to provide a superimposition display which includes superimposition of any eight second interval of analog data, in full size, eight second ECG strip display.

The system of the present invention is also capable of generating a full disclosure (FD) reports, including a monitoring period summary report which is downloaded into the system within approximately the first minute of rewinding of the cassette tape in the playback deck interface of a cassette recorded on the ECG recorder described in the above-identified co-pending application.

BRIEF DESCRIPTION OF THE DRAWINGS

The above-noted and other features of the invention will be better understood from the following detailed description of the invention when considered in conjunction with the accompanying drawings, in which.

DETAILED DESCRIPTION OF PREFERRED EMBODIMENTS

Figure 1:
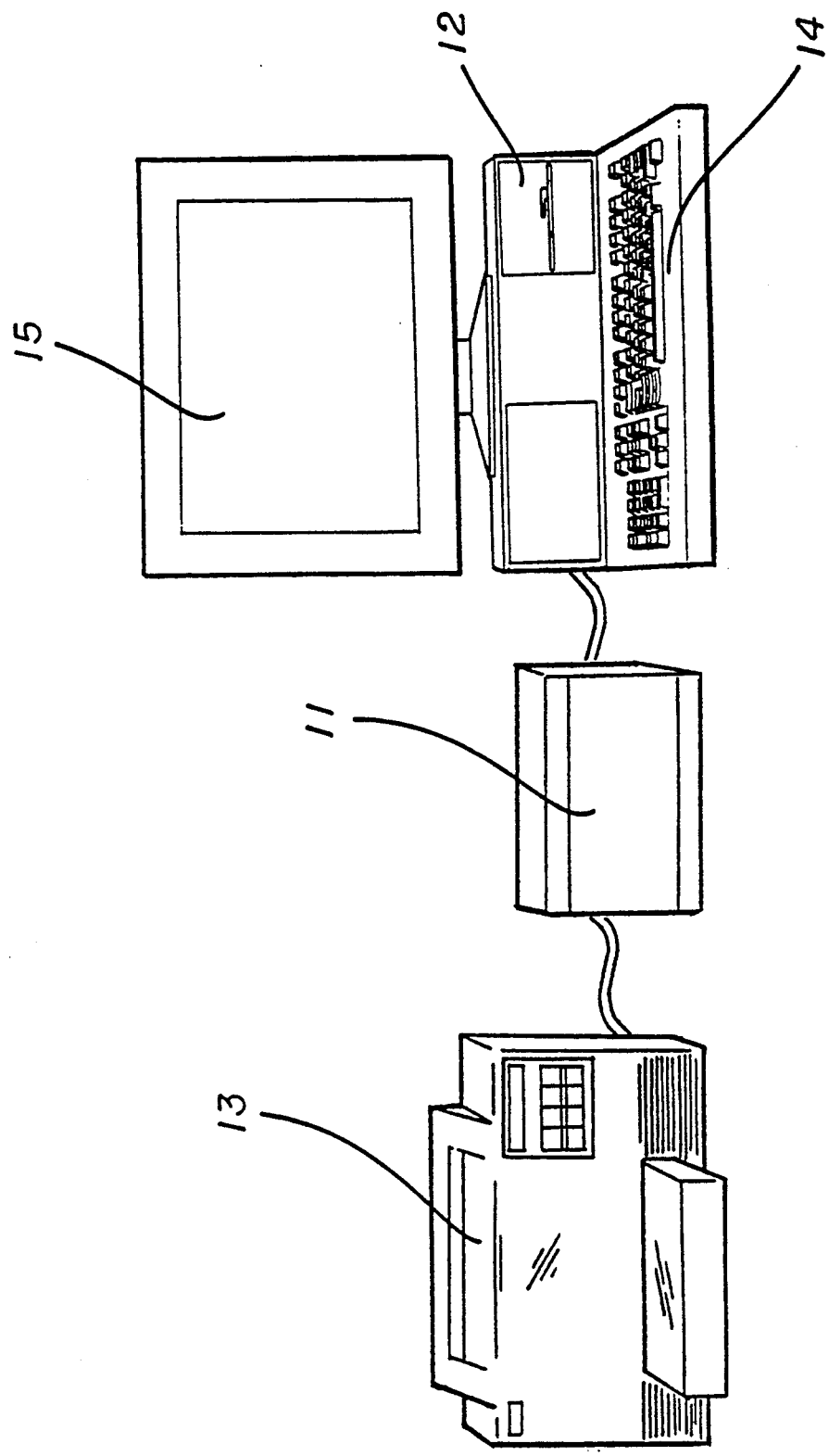
FIG. 1 shows a perspective view of an ambulatory ECG analysis system formed in accordance with the principles of the present invention.

In the exemplary drawings, used for purposes of illustration, an embodiment of an ECG analysis system made in accordance with the principals of the present invention is referred to generally by the reference numeral 10. The system 10 is part of an ECG monitoring system which includes the system 10 and an ECG recorder unit (not shown) such as that described in the above-identified co-pending application.

The analysis system 10 is primarily designed to receive information from a cassette tape, including analog ECG signal data and digitally recorded analysis data related thereto, and allow analysis, editing, and reporting of the information for use by medical personnel in diagnosis, assessment of the effacy of treatments such as drug therapy, and analysis of pacemaker performance on a patient's heart.

As best shown in FIG. 1, the analysis system 10 of the present invention includes a Playback Deck and Interface (PDI) 11 which is a relatively compact, four track, four channel tape playback deck, and a general purpose multiport interface which links the PDI 11 to a Dedicated Data Analysis Unit (DDAU) 12. The PDI 11 operates generally to rewind a standard tape cassette and play it back at high speeds to download recorded information into the DDAU 12. The PDI 11 converts the analog ECG signals into digital signals prior to downloading, and can perform other processing steps on the ECG and digital data received from the cassette tape as will be explained in detail below.

Further, when cassette tapes recorded by the ECG recorder as described in the above-identified co-pending application are processed through the PDI 11, monitoring period summary information can be downloaded into the DDAU 12 while the cassette tape is in the rewind mode for immediate reporting to the system operator.

The PDI 11 is designed to allow downloading of up to two channels of ECG analog data, whether recorded by the ECG recorder of the above-identified co-pending application, or by a prior art ECG recorder. Further, the PDI 11 will download and process up to two channels of digital information, such as would be included on a cassette tape recorded by the ECG recorder of the above-identified co-pending application.

The DDAU 12 functions as the primary power unit of the system 10 and includes a main digital processor, a printer interface board for linkage to the printer 13, and a power supply. The DDAU 12 controls the downloading editing and other manipulative operations on the ECG data received from the PDI 11, and subsequently generates summary and full disclosure (FD) reports related to the collected data.

If desired, the DDAU 12 may be a computer of the type commonly designated as a personal computers (PC). The DDAU 12 preferably includes an 80 megabyte power drive, a 1.2 megabyte floppy disk drive, and a 2 MB RAM memory. An example of a PC useful for the purposes of the present invention is a Model 302 386EC computer manufactured by the Entail Corporation, however other similar PC-type computers may also be used. Information downloaded from the PDI 11 into a PC of the above general type would preferably be recorded onto a hard disk, allowing the data to remain resident in the unit until another cassette tape is downloaded. Further, for the convenience of the user, floppy disk drives can be incorporated into the DDAU 12 in order to allow data to be transferred onto a disk for permanent storage.

A keyboard 14 such as an AT-style keyboard adapted for easy data entry is linked to DDAU 12. An example of a keyboard useful for the purposes of the present invention is a Model 101 alphanumeric AT-style keyboard manufactured by Keytronic. Similarly, a printer 13 is also linked to the DDAU 12 for allowing printing of data and generated reports. Any type printer 13 may be used in conjunction with the present invention, however a high resolution laser printer is preferred for rapid and precise reproduction of ECG wave forms. An example of a printer 13 useable with the analysis system 10 of the present invention is a LASERJET III printer manufactured by Hewlett-Packard If desired, a scope or monitor 15 may be included as part of the system 10 and linked with the DDAU 12 in order to allow visual review of real-time wave forms, and to simplify data editing and report generation. The monitor 15 preferably includes an audio output unit for allowing ECG signals to generate tones which change depending on the amplitude of the signal to alert the medical personnel of heart rate and beat morphology changes.

Further, if desired, the monitor 15 and the DDAU 12 may be adapted with a high resolution color graphics board to allow display of ECG data in varying colors for purposes of beat rhythm classification, multiple beat superimposition, and for other purposes relating to editing, displaying, and generating reports as will be explained in more detail below.

GENERAL OPERATION

The analysis system 10 of the present invention can operate in a variety of modes depending on the needs of the medical worker performing the ECG analysis, and also depending on the type of data (either analog or analog/digital) recorded on the cassette tape to be analyzed. The modes of operation are generally as follows: 1) data entry and end of monitoring period summary report generation; 2) tabular and wave form editing; and 3) superimposition editing.

Data Entry and Summary Report Generation

The data entry and end of monitoring period summary report generation is automatically initiated immediately upon the insertion of a cassette tape into the PDI 11. When the tape is properly inserted, the DDAU 12 requests the medical worker to identify the tape as containing analog ECG signal data only, or analog ECG signal data along with digital real-time analysis data. If the medical worker indicates that the tape contains only analog ECG signal data, the system 10 will perform its own complete analysis of the data without attempting to search for or correlate digital analysis data from the tape. This will be explained momentarily.

If the medical worker indicates that the tape includes analog ECG signal data and digital analysis data, such as would be the case if the cassette was recorded on the recorder of the above-identified co-pending application, the tape will immediately begin to rewind, and the end of monitoring period summary information will be downloaded during the rewind operation into the DDAU 12 and summary report generation will be immediately initiated. Details related to the method of recording the data onto the tape to allow for downloading of summary information during rewind of the tape are included in the above-identified co-pending application. The DDAU 12 will then request particular patient information data including patient identification and medical background, cassette tape identification and recording information, patient medication and/or other medical information, clinical parameters relative to the monitoring period, diary entries relating to patient events recorded on the tape, indications, physician information, and other desired background information.

Once the data entry is complete, the DDAU 12 requests the medical worker to indicate whether the end of monitoring period summary report should be printed immediately, and/or whether other specialized reports generatible from the already downloaded summary information are desired. These other reports may be specialized reports such as histogram reports, arrhythmia reports, S-T episode reports, morphology examples, other user selectable examples, etc.

Once the end of monitoring period summary and/or other specialized reports have been selected for printing, and the cassette tape has been completely rewound, the DDAU 12 then asks the user if it is desired to run the tape forward through the playback deck to download the complete information collected during the monitoring period. If so, the system 10 initiates forward review of the tape to convert the analog ECG signal data to digital data and download it along with the analysis data onto a hard disk in the DDAU 12.

Upon downloading of the data from the cassette tape, the DDAU 12 can analyze the analog ECG signal data in a manner similar to the analysis performed by the recorder as described in the above-identified co-pending application.

This is useful when a tape which has no analysis data thereon is used in the system 10. However, it should be noted that the system 10 may also re-analyze ECG data received from a tape which already includes analysis data if the operator so chooses.

The DDAU 12 analysis can be broken down into four general phases. The first phase being a calibration phase in which the PDI 11 compares the apparent gain of the initially recorded calibration pulses on the cassette tape to the known gain at which the calibration pulses were recorded. The PDI 11 then sets the apparent gain (the gain which is being played back from the cassette tape) to match the known gain (the gain at which the calibration signals are actually recorded) to calibrate itself with respect to the particular cassette tape. The remainder of the data on the tape will thereafter be recorded onto the DDAU 12 hard disk at its actual gain.

The second phase of the re-analysis is the learn phase, which is defined as the period of time which is used to establish a beat detection threshold (used to identify whether or not a particular signal should be classified as a heart beat), achieve a stable heart rate, and generate a "normal" beat for use as a template for later beat classification. Once the template is generated, it is continuously updated during analysis of the analog ECG signal data.

The third phase of the analysis process is the classification phase, in which each beat is first classified and annotated as representing any one of several possible morphology types.

The fourth and final phase of the analysis process is the report generation phase, in which minute, hour, and monitoring period summaries of beat classification and rhythm types are compiled and stored for later manipulation, editing, and report generation by the user.

The first, second and third phases of the analysis process are carried out substantially as described in the above-identified co-pending application. The fourth phase of the analysis process of the system 10 of the present invention will be discussed in more detail below in conjunction with a more detailed description of the operation of each component of the system 10.

The PDI 11 includes two major components: 1) a playback deck which performs the basic functions related to inputing data to the DDAU 12 from the cassette tape (i.e. tape motion, analog data conversion, digital data acquisition, etc.); and 2) an interface or "link", which transfers power, operating commands, and data signals between the playback deck and the DDAU 12.

The playback deck is one of several self-contained modules that is connected to the DDAU 12 to form the entire apparatus of system 10. The playback deck processes the ECG and digital data signals which have previously been recorded on the cassette tape during the monitoring period and sends them through the interface to the DDAU 12. Most commonly, when a cassette tape has been processed by the ECG recorder of the above-identified co-pending patent application, there will be four tracks of information recorded onto the cassette. Tracks 1 and 2 will include analog ECG signal data, Track 3 will include digital data information relating to the occurrence of each beat (ECG complex) and the ECG recorder's real-time analysis (RTA) of beat arrythmia and annotation of each detected beat according to arrythmia analysis determination of the beat morphology, and Track 4 will include further digital information including summary information, event marker status, real-time clock (RTC) information, etc., as has been explained in the above-identified co-pending application.

The playback deck generally consists of two printed circuit boards, (a digital board and an analog board) and a tape transport mechanism. The playback deck receives operating commands through the interface or "link" from the DDAU 12. The playback deck microprocessor receives and interprets these operational commands and controls the analog board and the tape transport mechanism accordingly.

Figure 2:
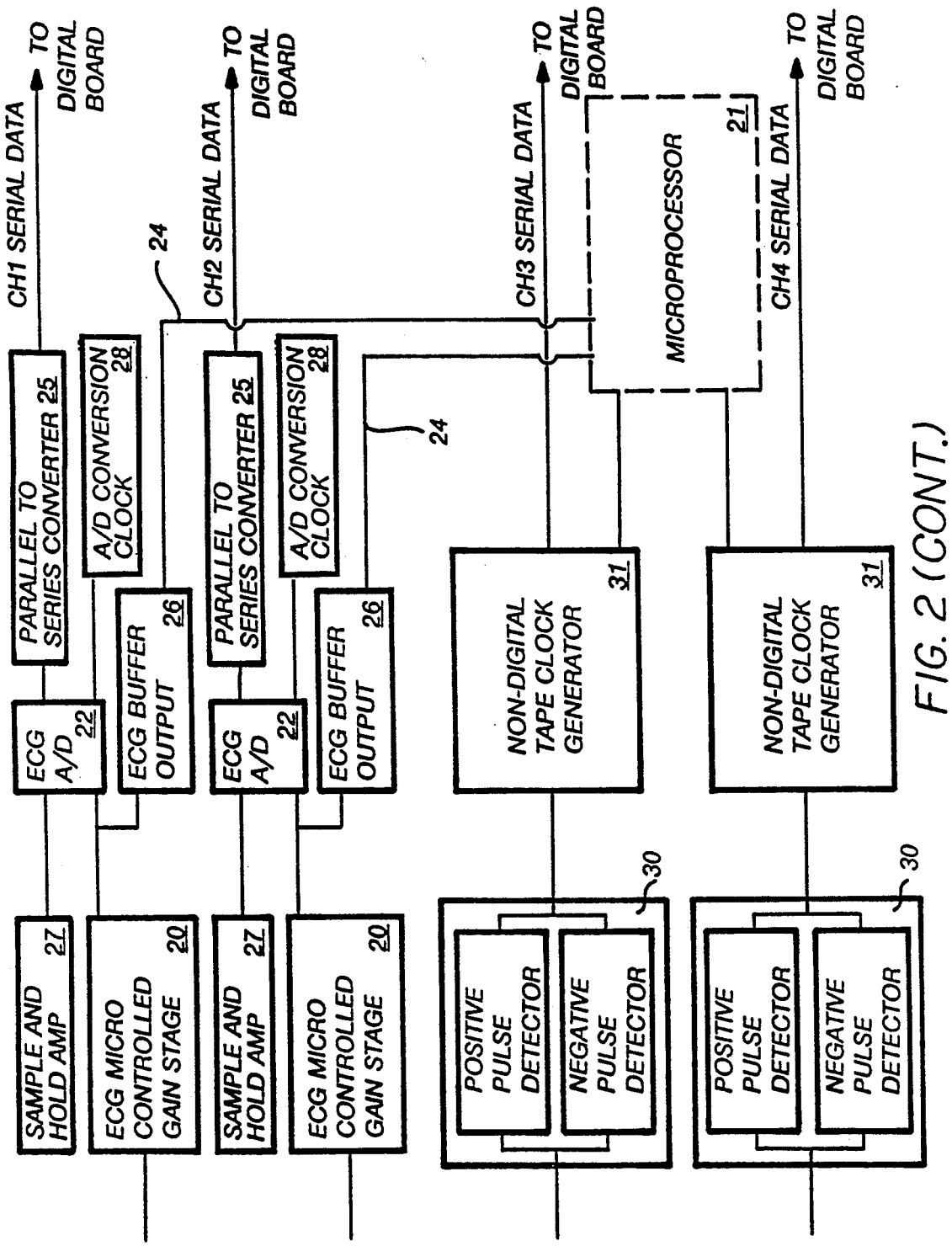
FIG. 2 is a block diagram of the analog portion of a playback deck of the ambulatory ECG analysis system following the principles of the present invention.

As best shown in FIG. 2, the cassette tape 16 is read through a tape head 17 and the signals for each of the four channels of data are each passed through tape head preamplifiers 18 and 19. The ECG amplifiers 18 are designed to remove any DC bias from the analog signals in a well known manner and thus differ from amplifiers 19 in this respect.

The pre-amplifiers 18 and 19 are directly coupled to the tape head thus ensuring excellent low frequency response for faithful reproduction of the analog ECG signal data. This is extraordinarily important for the intended use of the present invention in that several very important analyses performed on the analog ECG signal data include analyses directed to the form or shape of specific segments of the heart beat wave form which constitutes a part of the analog ECG signal. For example, the shape of the ST segment of the heart beat wave form is of particular importance in determining ischemia, or insufficient blood flow to the heart.

The ECG microcontrolled gain stage 20 is provided to allow for variations in ECG signal amplitude. They are designed to compensate for variations in recorder gain, cassette tape manufacturer variations, and preamplifier gain. This is accomplished by using the eight bit VD converters 21 as the variable gain control.

The gain is controlled by the microprocessor 21 which has the capability of sampling the ECG data. When a new cassette tape 16 is inserted in the tape transport (not shown) of the playback deck, the microprocessor 21 initiates rewind of the tape 16 to the beginning. Any reverse format data on the tape 16 is downloaded during rewind to the DDAU 12. After rewind, the microprocessor 21 initiates forward motion of the tape to begin analysis of the forward formatted information thereon.

Tapes recorded by the above-identified co-pending application process begin with a series of calibration pulses. Since the calibration pulses are of known amplitude, the microprocessor can calculate the value that (when stored in the A/D 22) provides the desired gain. For example, it may be desired to match the gain of the information as stored with the known gain of the information as recorded. This is accomplished by matching the gain of the calibration pulses as received from the tape with the known gain of the calibration pulses as they were recorded. With this method of gain control, a variety of gain settings can be made standard on the analyzer 10 (i.e. x.5, x1, x2, x4) in addition to any special gain settings that may be required or useful in the arrythmia analysis.

The ECG gain control stage 20 receives data from the ECG amplifier 23 and interfaces directly with the microprocessor through a data bus 24. The result and output of the ECG gain control stage is the sealed (calibrated) ECG signal which is tied to a current two voltage converter 25. The interface with the microprocessor 21 is through an ECG buffer 26.

To provide for faithful conversion of the ECG data, a "sample and hold" amplifier 27 has been provided. This ensures that the ECG signal is stable during the A/D conversion process. The sample and hold input signal comes from the gain control stage 20 and is controlled by the A/D converter 22. The ECG buffer output through data bus 24 to the microprocessor 21 ensures that the data routed to the A/D converter 22 is not perturbed by the digital noise from the microprocessor 21.

The A/D converter 22 converts the ECG data into eight bit parallel data at a 30.72 KHz rate. The A/D conversion clock 28 is set at 491.52 KHZ and is generated from the digital board where the sample clock (not shown) is also generated. The sample rate frequency is based on a 256 Hz real-time sample rate and a tape speed of 120 mm/second (120 times real-time).

The A/D converter 22 outputs to the parallel/serial converters 25 to convert the eight bit parallel data to serial data to allow its transfer from the playback deck through the interface to the DDAU 12.

Returning now to the tape head 17, channels 3 and 4 of the cassette tape have been recorded with digital information using the "return to zero" (RZ) in coding, as has been explained in applicant's above-mentioned co-pending application. The method was chosen for its ease of use and its sensitivity to tape speed variations.

Data from channels 3 and 4 from the tape head 17 pass through the digital track tape head pre-amplifiers 19 and the digital data gain adjustable amplifiers 29 to comparitors 30 and through tape clock generator 31 to convert the pulses from the tape into standard data pulses suitable for analysis. Each data channel has a comparitor 30 which is used to convert positive flux changes and negative flux changes on the tape into useable digital data information.

If a tape is played in the playback deck which contains no information on channels 3 and 4, such as a tape recorded on a prior art recorder which includes only analog ECG signal data, and which does not provide real-time analysis of the ECG signals circuitry (not shown) is provided in the tape deck to perform simple single channel beat detection similar to that described in the above-mentioned co-pending application.

The channel to be analyzed is automatically selected by the microprocessor after determining which channel has the largest amplitude ECG signals.

The playback deck performs all of the digital functions required by the playback deck by separating the digital circuitry from the analog circuitry, the integrity of the analog ECG data can be maintained since digital data and microprocessor noise are substantially isolated from the analog board.

The heart of the playback deck is the microprocessor 21, which is preferably a microprocessor such as a model 68AHC11 by Motorola.

Figure 3:
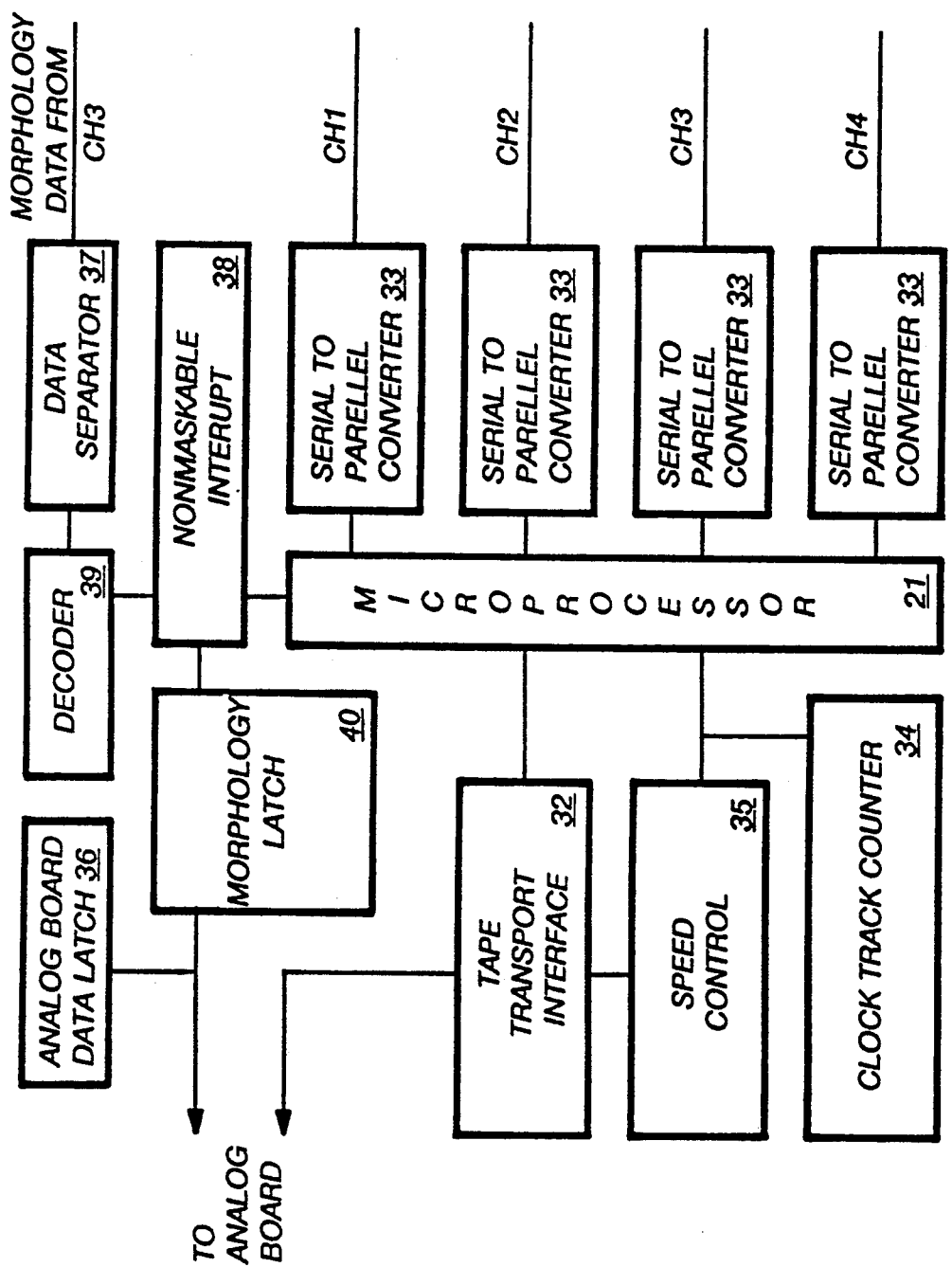
FIG. 3 is a block diagram of the digital portion of a playback deck of the ambulatory ECG analysis system following the principles of the present invention.

Referring now to FIG. 3, the tape transport interface 32 is capable of providing a variety of tape speeds, and is also capable of signalling the presence of a tape in the playback deck, including motion and direction of the tape. The digital data serial/parallel converters 33 convert the serial digital data from the analog board into parallel data for input to the microprocessor 21.

The clock track counter 34 is used only when a tape has been recorded on a prior art system instead of the ECG recorder of the above-mentioned co-pending patent application. The clock track counter 34 is controlled by the clock in the DDAU 12 as will be explained below, and actually constitutes three separate counters. One counter being configured as a "one shot" counter which is used to keep track of partial minutes when starting the tape. The second counter is used to count full minute transitions. Both the first and second counters flag the minute transition by interrupting the microprocessor through a periodic interrupt, in the manner as has been explained in the above-mentioned co-pending application.

The third counter is sampled on a regular basis to determine the actual real-time tape speed (real-time tape speed being a function of the tape speed when the data was recorded). The counter is sampled at regular intervals and variations in the expected results are used to calculate and continuously update an error correction value to be output to the tape transport speed controller 35. Since the clock recorded on the tape 16 is a 32 Hz clock track, and since the tape 16 is played back in the playback deck at a high rate of speed, (from 60 to 240 times its recorded speed) preferably at 120 times its recorded speed, a sensed clock track signal is going to be 32 times 120 Hz or 3840 Hz. The actual clock track frequency being received by the playback deck is sampled at regular intervals and variations in the actual frequency with respect to the expected frequency are used to calculate and update the error correction value sent to the tape transport speed control 35. The tape transport speed control 35 provides an input into the tape transport mechanism used to make fine adjustments to the tape playback speed. The speed control 35 can compensate for approximately a plus or minus 10% speed variation between the actual data reception speed and the expected reception speed, by adjusting the voltage level input into the tape transport mechanism (not shown).

The microprocessor 21 on the digital board is used as the central component of the spaced control system. The microprocessor 21 senses the current tape speed at regular intervals by counting the clock track pulses from the tape. After computing the tape speed error, by comparing the actual count to the expected count (the count expected during a 32 Hz clock signal accelerated at 120 times its recorded speed) the microprocessor 21 computes the tape speed error, and a correction value is sent to the speed control 35 which controls the voltage level input to the tape transport interface 32 which translates to a tape speed correction of up to a maximum of plus or minus 10%. The signal is filtered by a low pass filter in the interface 32 to allow smooth tape speed operation of the tape transport mechanism.

The speed control 35 of the present invention has two advantages over prior art systems. First, it eliminates the effects of tape stretching which may have occurred since the recording was made, and secondly it can eliminate errors which may have occurred in the actual speed at which the tape was recorded. Since the recording characteristics of each recorder used for ECG recording are slightly different, it is difficult if not impossible for each tape to have been recorded at exactly the same speed. Especially since the recording speeds for ECG monitoring on cassette tapes are usually extremely slow (in the neighborhood of 1 millimeter per second). By measuring the apparent clock frequency against its expected frequency as the tape is played, the tape transport speed can be adjusted to compensate for any speed discrepancy. Such discrepancies may be introduced into the tape in various ways such as stretching caused by starting and stopping the tape at very high speeds, temperature changes, variations in tape speed between recorders, etc.

The analog data latch 36 passes digital information from the microprocessor 21 to the analog board. This helps reduce microprocessor noise in the analog data by making the data lines on the analog board static, unless the microprocessor 21 specifically addresses the analog board. Data to be sent to the analog board is first written to the analog data latch 36 prior to be passed on to the analog board. The return-to-zero data separators 37 receive data from the analog board relating to channels 3 and 4 and separates digital analysis data from the synchronous clock data for each of the two channels (channel 3 and channel 4).

Once the digital morphology data of Channel 3 has passed through the data separator 37, it is decoded and made available to the microprocessor 21 through a nonmaskable interrupt (NMI) 38. The decoder 39 converts the serial digital morphology data to parallel decoded morphology data through a multiplexer. The data is then latched at morphology latch 40 and the NMI is generated and sent to the microprocessor 21. If the playback deck of the present invention is used with tapes which contain no digital analysis information, the multiplexer of the decoder 39 remains set at a default value, which is sent to the microprocessor in lieu of the decoded morphology data.

Tabular and Waveform Editing

Figure 4:
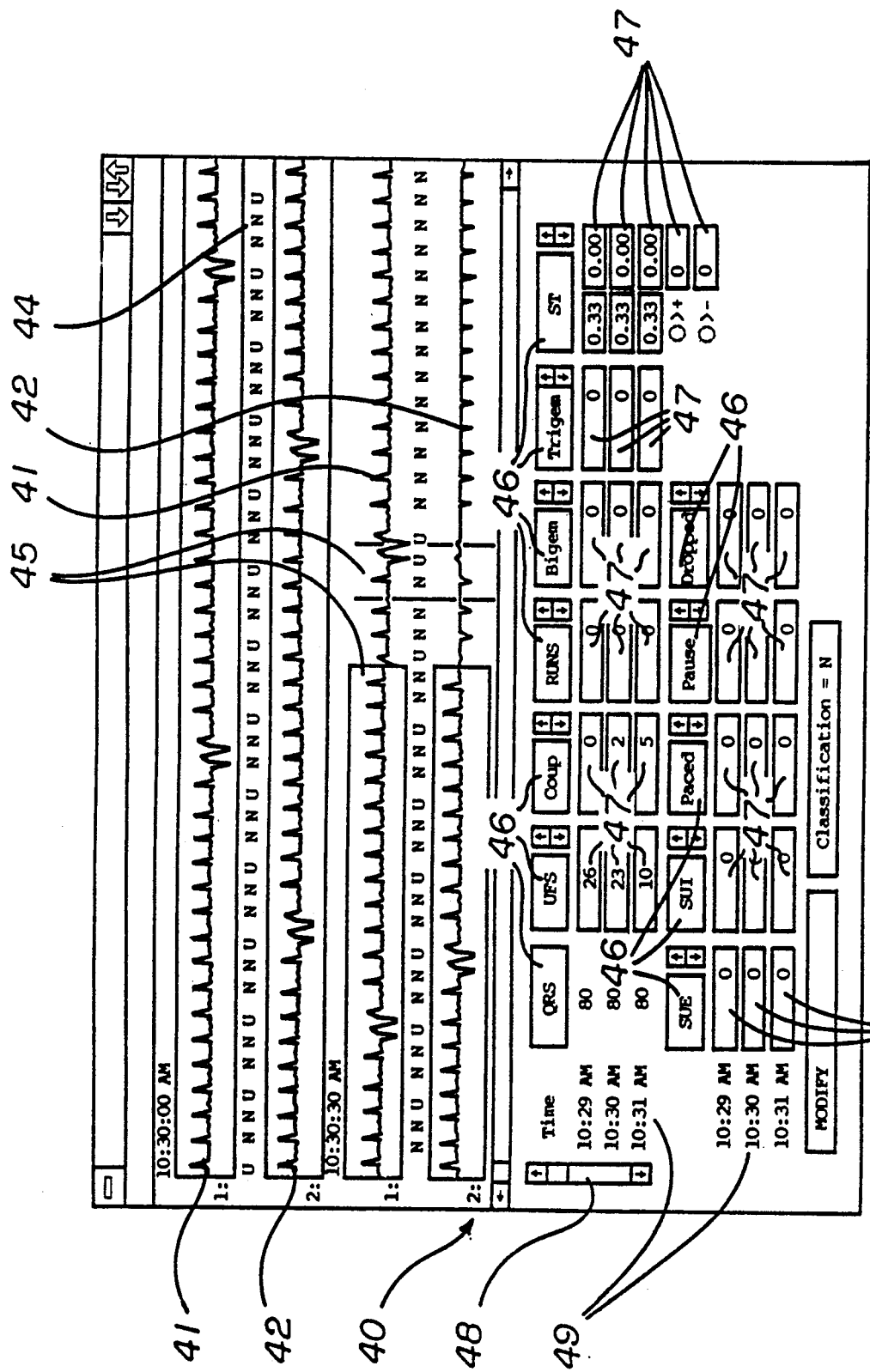
FIG. 4 is a minute-by-minute ECG template of the ambulatory ECG analysis system formed in accordance with the principles of the present invention including examplary ECG data thereon.

If the system 10 of the present invention includes a monitor 15, data relating to both the analog ECG signals and digital real-time analysis data can be edited by the operator in an interactive manner through input to the DDAU 12 by the keyboard 14 through the use of a minute-by-minute ECG display template, shown as element 40 in FIG. 4. (The template 40 includes sample data written thereon to aid in explanation of the template's function.)

As can be seen, the template 40 is designed to accommodate two lines 41 and 42 respectively representing channels of analog ECG data, which extend horizontally across the template 40 in two segments, each representing a 30 second period of analog ECG signals as received by the ECG recorder. Time data 43 is also transferred to the template 40 to indicate the time period in which the ECG data 41 and 42 was collected by the ECG recorder.

Also transferred to the template 40 are annotations 44 which represent analysis results of each heart beat waveform detected on the ECG lines 41 and 42 as performed by the ECG recorder as explained in the above-mentioned co-pending patent application. Analysis resulting in a heart beat waveform receiving a "normal" designation show on the template 40 with the capital letter "N" adjacent thereto. All heart beat waveforms designated by the recorder analysis as being "abnormal" are designated with the capital letter "V". All heart beat waveforms designated as being responsive to a pacemaker pulse are designated with the letter "P".

Highlighting 45 is also placed onto the template 40 over predetermined sections of the ECG lines 41 and 42 to designate particular abnormal beat rhythms such as couplets (a normal and abnormal beat) bigeminal beats (a series of couplets), trigeminal (a normal, abnormal, normal or similar series which repeats), runs (a series of abnormal beats including more than two consecutive abnormal beats), dropped beats (a pause equal to approximately the absence of a single beat), pauses (absence of beats for a period of time exceeding one normal beat), and superventricular tachycardia (a series of rapidly occurring beats).

If the monitor 15 used in conjunction with the present invention includes color capability, a range of colors may be used for highlighting 45 in order to distinguish between different types of abnormal beat rhythms. It should be noted that the highlighting 45 is intended only to draw attention to the abnormal beat rhythms and is not intended to obscure the operator's view of the ECG signals in lines 41 and 42. The remainder of the template 40 includes a schematic which in part represents keys present on the keyboard 14 which can be employed in editing ECG data. For example, each box 46 described by the template 40 has designated therein a particular feature of the ECG data which may be reviewed, analyzed, and/or edited by the operator. Each box 46, if desired, may be color coded to match color coding of corresponding operating keys on keyboard 14 in order to simplify the editing procedure.

Below each box 46, information boxes 47 allow placement of data corresponding to the particular feature of the data identified in the box 46. The data is displayed for review and editing by the operator. To the extreme left of the tabulating boxes 47, the template 40 includes a vertical scroll bar 48 and time display 49. The times are written over the template 40 into the time display area 49 represent the previous minute, the selected minute, and the subsequent minute of ECG data displayed above on the line display portion of the template 40. Minute-by-minute scrolling through the ECG data can be accomplished through manipulation of a cursor or mouse as described above.

The operator can review proceeding or subsequent minute ECG segments through a simple command entered to the DDAU 12 such as through the keyboard 14 or a mouse (not shown) to cause ECG lines 41 and 42 to scroll forwards or backwards through minute-by-minute of ECG data.

To edit a particular data feature, the operator merely accesses the data feature through the keyboard 14 by the proper key as designated in the desired box 46 on the template 40, and then modifies the data as desired. For example, to insert or modify a beat annotation 44, the operator merely identifies the particular beat annotation 44 (such as by designating it with the cursor) and then enters the new annotation 44 as desired.

An operator may delete an entire beat from the ECG lines 41 and 42 in a similar manner by indicating the particular beat desired (such as by moving the cursor to the beat) and actuating the delete command from the keyboard. Similarly, beat rhythm designations and highlighting 45 corresponding thereto can be edited.

As can be seen, the template 40 of the present invention can be used as an interactive tool between the user and the DDAU 12. The template 40 can be generated with the aid of any number of well known software packages, such as for example, the software package marketed under the trademark of WINDOWS.

Superimposition Editing

Figure 5:
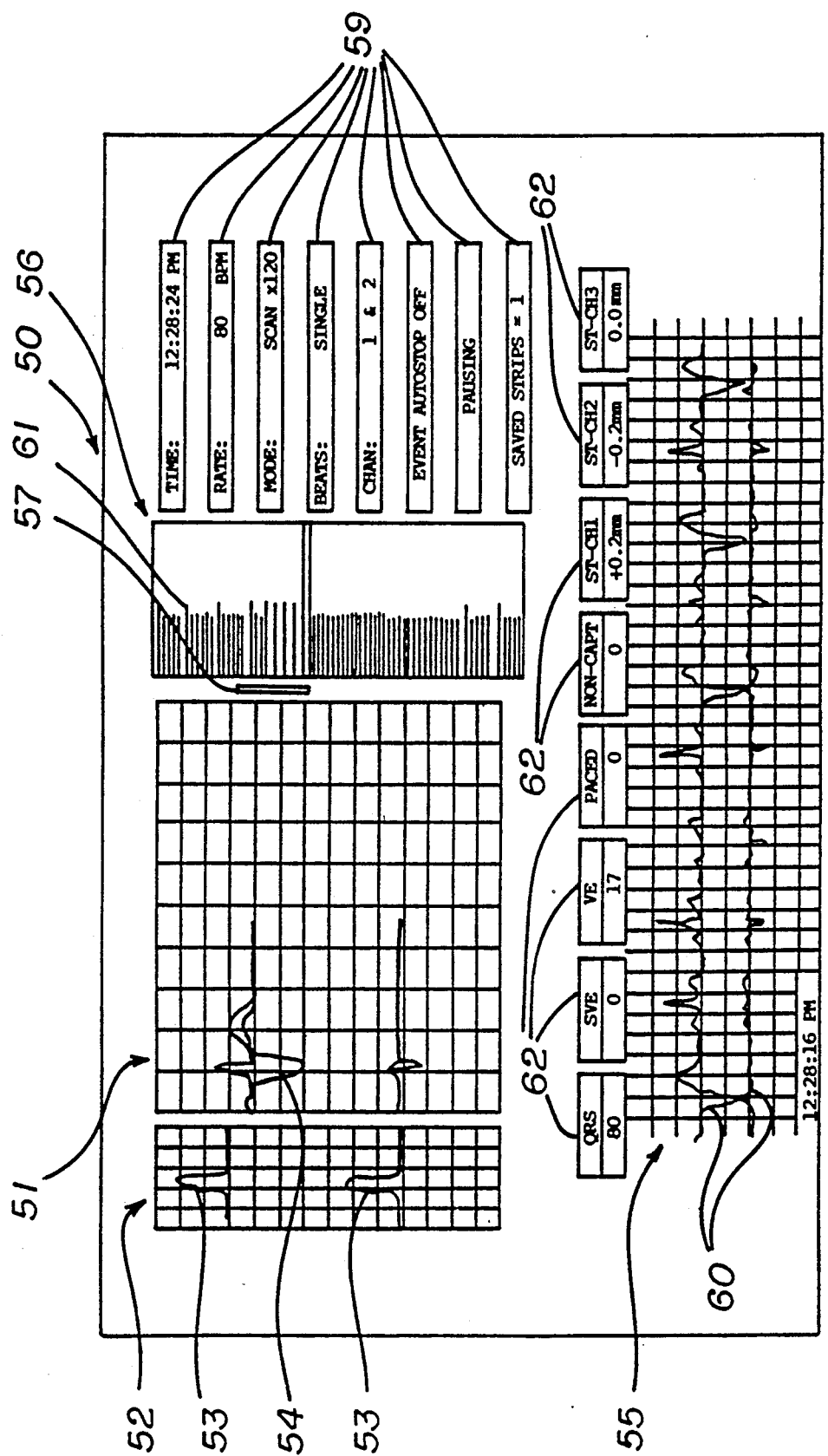
FIG. 5 is a superimposition template of the ambulatory ECG analysis system formed in accordance with the principles of the present invention including exemplary ECG data thereon.

A superimposition template 50 is shown in FIG. 5 (and includes example ECG data transferred thereon for simplification explanation of the template's function). The template 50 allows viewing of ECG waveforms in order to identify significant changes in heart beat waveform patterns. The template 50 allows simultaneous display of single or dual channel full size beat waveforms 54 to be viewed in the superimposition box 51 thereof. A calibration pulse reference box 52 is located directly adjacent to box 51 and allows display of reference calibration pulses 53 in a position adjacent the superimposed beats 54 corresponding to the channel from which the calibration pulse 53 was extracted. The superimposed ECG waveforms 54 in the superimposition box 51 correspond to the ECG waveforms shown in the "8 second strip" window 55.

The "minute" window 56 of the display 50 includes a bar graph representation of each beat occurring in a sixty second time period and includes an "8 second" marker 57 which can be moved in the vertical direction along the "minute" window 56 and also corresponds to the 8 second ECG line 60 in the 8 second strip window 55 and the 8 seconds of superimposed ECG heart beat waveforms 54 in superimposition box 51.

Each bar 61 in the minute window 56 represents a heart beat waveform, with the spacing between each bar 61 representing the interval between each beat. If desired, the bars 61 may be color coded in order to denote the particular annotation (normal, abnormal, paced) assigned to the beat. The minute window 56 also includes a cursor 58 which indicates the end of the current ECG data scanned.

Boxes 59 of the template 50 are used to present statistical information and other particulars of the ECG information present in boxes 51, 55 and 56. Similarly, boxes 62 display specific statistics related to the ECG information in the 8 second strip box 55.

In use, the operator can allow ECG data to pass through the template 50 in a rapid manner and review the information as it is displayed. When desired, the operator can pause or "freeze" the information on the template 50 for detailed review. As explained above, when the template 50 is pause, the data displayed in minute window 56 includes the last minute of data scanned, starting with the most recent data being displayed above cursor 58, through the oldest data of the minute located below the cursor 58. As data moves through the template 50, the cursor 58 moves vertically through the minute window 56 from top to bottom thereof, leaving the most recent data therebehind as it passes, and writing over the oldest data.

In the pause mode, the operator can move the 8 second marker 57 vertically along the minute window 56. Movement of the marker 57 causes the 8 seconds of information directly adjacent thereto in minute window 56 to be displayed as superimposition data 54 in superimposition box 51, and as an 8 second strip 60 in box 55. In this way, an operator can rapidly advance through data until a particular set of data is approached or has been recently passed (within a minute of data) and then pause the data. The operator can then move marker 57 to any position within the last minute of scanned data to position 8 seconds of data in the superimposition window 51 and the 8 second strip window 55. In this manner the operator can narrow review down to specific areas of the ECG data very rapidly.

Once the operator has identified a particular set of ECG data, the data located in 8 second strip window 55 can be sent to the printer 13 to be printed to generate a permanent record of the 8 second strip of data. The operator can then continue through rapid review of ECG data by continuing to scan through template 50 until it is desired to pause again for more detailed and extended review or printing of an 8 second strip of data.

As it is evident, template 50 can be generated by means of existing software packages in substantially the same manner as template 40 shown in FIG. 4.

Report Generation

The system 10 of the present invention is capable of generating a plurality of reports of the ECG data received from the cassette tape of the ambulatory recorder and also from its internal analysis and editing. There are basically two categories of report generation which can occur in the system 10. The first is an end of monitoring period summary which was downloaded to the system 10 from the cassette tape 16 if the cassette tape had been used in the ambulatory recorder disclosed in the above-mentioned co-pending application. The end of monitoring period summary report is compiled by the recorder and recorded in reverse format onto the tape 16 as explained in detail in the above-mentioned co-pending application. The PDI 11 reads and downloads this information while the cassette tape 16 is being rewound therein, and the DDAU 12 can initiate printing of the report by the printer 13 prior to the completion of rewinding of the tape 16 by the PDI 11.

An example of the end of monitoring period summary report is annexed hereto as part of the Appendix, and includes pages 1-A through 5-A. The summary reports can include a narrative report, an hourly tabular report, an ST level report, and a histogram report.

The second category of reports generatable by the system 10 of the present invention include retrospective reports which can be generated and printed any time after complete downloading of the information from the cassette tape 16. The above-identified end of monitoring period summary reports can again be generated and printed if desired, further, other reports as examplified in the Appendix on pages 6-A through 24-A can be produced. These reports include; a full disclosure report, a summary report, an hourly arrythmia tabular report, an ST trend report, a patient event summary report, a patient diary report, a histogram of R-R intervals, isolated morphology examples, user selected eight second strips, an ST level report, arrythmia sample strips, and a full disclosure arrythmia report.

It will be apparent from the foregoing, while particular embodiments and characteristics of invention have been illustrated and described, various modifications can be made thereto without departing from the spirit and scope of the present invention. Accordingly, it is not intended that the invention be limited, except as by the appended claims.

Quinton Q960 Superimposition Scanner
Quik-Summary™ Narrative Report

| | | |
|---|---|---|
| SEATTLE CARDIOLOGY CLINIC | Patient: Smith, John | I.D.#: 550-78-1234 |
| 2121 TERRY AVENUE | Address: 1231 Main Street | Record Date: 11/05/90 |
| SEATTLE, WA 98121 | Seattle, WA 98121 | Analysis Date: 12/03/90 |
| (206) 223-7373 | Telephone: (206) 555-1111 | Referring M.D.: Dr. Blackman, Bellevue, WA |
| X362-38100 | Birth date: 10/10/20 | Pacemaker: Medtronic   Type: VVI |
| | | Implant Date: 10/10/89 |

| | | |
|---|---|---|
| Hook-up Location: OFFICE | Age: 70  Sex: Male   B.P.: 122/078 | Medicare #: N.A. |
| Hook-up Tech: DAVE | Height: 62"   Weight: 190 | CPT CODE: 93224 (Q-019) |
| Recorder: Q-CORDER 932, #4 | Electrode Placement: CM5, CM1, MCL | Insurance: CIGNA |
| Data Quality: Good | Analysis Tech: GEORGE | Policy #: 0256789 |
| Medications: ADVIL, DIGITALIS, LIDOCAINE, NORPACE | Indications: CARDIAC ARRHYTHMIAS, CHEST PAIN / ANGINA, PACEMAKER | Comments: FEELS FINE TODAY. HAD CHEST PAIN YESTERDAY. DID NOT SLEEP WELL. |

BASED ON DUAL CHANNEL 24 HOUR AMBULATORY ECG ANALYSIS WITH SUPERIMPOSITION SCANNING AND CONTINUOUS FULL DISCLOSURE ECG PRINT-OUT.

The patient recording started at 07:35AM and was recorded for 24 hours, 0 minutes. 0 minutes of the recording contained excessive artifact. A total of 97154 normal beats were detected. The average heart rate was 68 BPM, with the minimum rate of 37 BPM at 06:56AM, and with the maximum rate of 170 BPM at 04:55AM.

There was a total of 1401 ventricular abnormal beats detected, equal to 1.4% of all the beats detected.

There was a total of 31 supraventricular ectopic beats detected which were more than 35% early.

Total paced beats were 20, equal to 0.0% of all the beats detected. There were 25 events of non capture, equal to 0.0% of all the beats detected. There were 16 events of failure to sense, equal to 0.0% of all the beats detected.

The total ischemic time with -1.0 to -1.9 mm ST level in any monitored channel lasted 2 minutes, with 2 episodes detected. The total ischemic time with -2.0 to -2.9 mm ST level in any monitored channel lasted 2 minutes, with 2 episodes detected. The total ischemic time with below -3.0 mm ST level in any monitored channel lasted 0 minutes, with 0 episodes detected.

The average ST level of channel 1 was 0.0 mm, with the minimum of -2.8 mm at 07:47AM, and with the maximum of 0.2 mm at 06:22AM. The average ST level of channel 2 was 0.0 mm, with the minimum of -0.2 at 07:35PM, and with the maximum of 1.0 mm at 07:47AM. The average ST level of channel 3 was 0.0 mm, with the minimum of -2.0 mm at 07:47AM, and with the maximum of 0.2 at 06:22AM.

5 patient indicated events occurred during the recording.

Final Interpretation: _____
_____
_____
_____

Physician Signature: _____ Date: _____
BARBARA GREEN, M.D.

Quinton Q960 Superimposition Scanner
Quik-Summary™ Hourly Tabular Report

Patient: Smith, John  
Record Date: 11/06/90

Patient ID: 550-78-1234  
Analysis Date: 12/03/90

| Hour | Heart Rate Min | Heart Rate Ave | Heart Rate Max | Total QRS | Total VE | Total SVE | ST Level Ch 1 min | ST Level Ch 1 ave | ST Level Ch 1 max | ST Level Ch 2 min | ST Level Ch 2 ave | ST Level Ch 2 max | ST Level Ch 3 min | ST Level Ch 3 ave | ST Level Ch 3 max |
|---|---|---|---|---|---|---|---|---|---|---|---|---|---|---|---|
| 07:35AM | 65 | 76 | 142 | 4357 | 60 | 7 | -2.8 | 0.0 | 0.2 | -0.2 | 0.0 | 1.0 | -2.0 | 0.0 | 0.2 |
| 08:35AM | 37 | 62 | 168 | 3748 | 107 | 2 | -0.3 | 0.0 | 0.0 | -0.2 | 0.0 | 0.0 | -0.2 | 0.0 | 0.2 |
| 09:35AM | 57 | 73 | 84 | 4403 | 14 | 0 | -0.3 | 0.0 | 0.2 | -0.2 | 0.0 | 0.0 | -0.2 | 0.0 | 0.2 |
| 10:35AM | 38 | 63 | 170 | 3819 | 110 | 2 | -0.3 | 0.0 | 0.0 | -0.2 | 0.0 | 0.0 | -0.2 | 0.0 | 0.0 |
| 11:35AM | 57 | 73 | 84 | 4411 | 0 | 0 | -0.2 | 0.0 | 0.2 | -0.2 | 0.0 | 0.0 | 0.0 | 0.0 | 0.2 |
| 12:35PM | 38 | 63 | 170 | 3813 | 110 | 2 | -0.3 | 0.0 | 0.0 | -0.2 | 0.0 | 0.0 | -0.2 | 0.0 | 0.0 |
| 01:35PM | 57 | 73 | 84 | 4414 | 0 | 0 | -0.2 | 0.0 | 0.2 | -0.2 | 0.0 | 0.0 | 0.0 | 0.0 | 0.2 |
| 02:35PM | 37 | 63 | 168 | 3810 | 112 | 2 | -0.3 | 0.0 | 0.0 | -0.2 | 0.0 | 0.0 | -0.2 | 0.0 | 0.0 |
| 03:35PM | 57 | 73 | 84 | 4420 | 0 | 0 | -0.2 | 0.0 | 0.2 | -0.2 | 0.0 | 0.0 | 0.0 | 0.0 | 0.2 |
| 04:35PM | 37 | 63 | 170 | 3803 | 110 | 2 | -0.3 | 0.0 | 0.0 | -0.2 | 0.0 | 0.0 | -0.2 | 0.0 | 0.0 |
| 05:35PM | 57 | 73 | 84 | 4427 | 0 | 0 | -0.2 | 0.0 | 0.2 | -0.2 | 0.0 | 0.0 | 0.0 | 0.0 | 0.2 |
| 06:35PM | 37 | 63 | 168 | 3798 | 110 | 2 | -0.3 | 0.0 | 0.0 | -0.2 | 0.0 | 0.0 | -0.2 | 0.0 | 0.0 |
| 07:35PM | 57 | 73 | 84 | 4431 | 0 | 0 | -0.3 | 0.0 | 0.2 | -0.2 | 0.0 | 0.0 | -0.2 | 0.0 | 0.2 |
| 08:35PM | 38 | 63 | 168 | 3797 | 112 | 2 | -0.3 | 0.0 | 0.0 | -0.2 | 0.0 | 0.0 | -0.2 | 0.0 | 0.0 |
| 09:35PM | 57 | 73 | 84 | 4431 | 0 | 0 | -0.3 | 0.0 | 0.2 | -0.2 | 0.0 | 0.0 | -0.2 | 0.0 | 0.2 |
| 10:35PM | 37 | 63 | 170 | 3797 | 112 | 2 | -0.3 | 0.0 | 0.0 | -0.2 | 0.0 | 0.0 | -0.2 | 0.0 | 0.0 |
| 11:35PM | 57 | 74 | 84 | 4432 | 0 | 0 | -0.2 | 0.0 | 0.2 | -0.2 | 0.0 | 0.0 | 0.0 | 0.0 | 0.2 |
| 12:35AM | 37 | 63 | 170 | 3792 | 110 | 2 | -0.3 | 0.0 | 0.0 | -0.2 | 0.0 | 0.0 | -0.2 | 0.0 | 0.0 |
| 01:35AM | 57 | 74 | 84 | 4438 | 0 | 0 | -0.2 | 0.0 | 0.2 | -0.2 | 0.0 | 0.0 | 0.0 | 0.0 | 0.2 |
| 02:35AM | 37 | 62 | 170 | 3784 | 110 | 2 | -0.3 | 0.0 | 0.0 | -0.2 | 0.0 | 0.0 | -0.2 | 0.0 | 0.0 |
| 03:35AM | 57 | 74 | 84 | 4446 | 0 | 0 | -0.2 | 0.0 | 0.2 | -0.2 | 0.0 | 0.0 | 0.0 | 0.0 | 0.2 |
| 04:35AM | 37 | 62 | 170 | 3780 | 112 | 2 | -0.3 | 0.0 | 0.0 | -0.2 | 0.0 | 0.0 | -0.2 | 0.0 | 0.0 |
| 05:35AM | 57 | 74 | 84 | 4449 | 0 | 0 | -0.2 | 0.0 | 0.2 | -0.2 | 0.0 | 0.0 | 0.0 | 0.0 | 0.2 |
| 06:35AM | 37 | 62 | 168 | 3775 | 112 | 2 | -0.3 | 0.0 | 0.0 | -0.2 | 0.0 | 0.0 | -0.2 | 0.0 | 0.0 |
|  | 37 | 68 | 170 | 98575 | 1401 | 31 | -2.8 | 0.0 | 0.2 | -0.2 | 0.0 | 1.0 | -2.0 | 0.0 | 0.2 |

Minimum ST Report

Channel 1

Channel 2

Channel 3

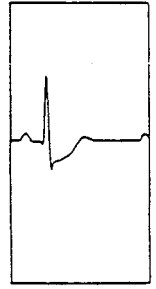

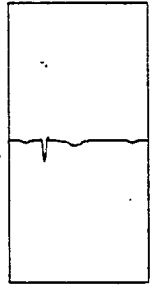

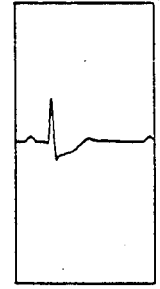

ST: -2.8 mm  
07:47AM

ST: -0.2 mm  
07:35PM

ST: -2.0 mm  
07:47AM

Quinton Q960 Superimposition Scanner
Quik-Summary™ Hourly Tabular Report

Patient: Smith, John
Record Date: 11/06/90

Patient ID: 550-78-1234
Analysis Date: 12/03/90

| Hour | Heart Rate Min | Heart Rate Ave | Heart Rate Max | Total QRS | Total VE | Total SVE | Total Paced | (%) Paced | Total Noncap | (%) Noncap | Total Failsense | (%) Failsense |
|---|---|---|---|---|---|---|---|---|---|---|---|---|
| 07:35AM | 65 | 76 | 142 | 4357 | 60 | 7 | 5 | 0.1 | 0 | 0.0 | 10 | 0.2 |
| 08:35AM | 37 | 62 | 168 | 3748 | 107 | 2 | 0 | 0.0 | 0 | 0.0 | 0 | 0.0 |
| 09:35AM | 57 | 73 | 84 | 4403 | 14 | 0 | 15 | 0.3 | 24 | 0.5 | 6 | 0.1 |
| 10:35AM | 38 | 63 | 170 | 3819 | 110 | 2 | 0 | 0.0 | 0 | 0.0 | 0 | 0.0 |
| 11:35AM | 57 | 73 | 84 | 4411 | 0 | 0 | 0 | 0.0 | 0 | 0.0 | 0 | 0.0 |
| 12:35PM | 38 | 63 | 170 | 3813 | 110 | 2 | 0 | 0.0 | 0 | 0.0 | 0 | 0.0 |
| 01:35PM | 57 | 73 | 84 | 4414 | 0 | 0 | 0 | 0.0 | 1 | 0.0 | 0 | 0.0 |
| 02:35PM | 37 | 63 | 168 | 3810 | 112 | 2 | 0 | 0.0 | 0 | 0.0 | 0 | 0.0 |
| 03:35PM | 57 | 73 | 84 | 4420 | 0 | 0 | 0 | 0.0 | 0 | 0.0 | 0 | 0.0 |
| 04:35PM | 37 | 63 | 170 | 3803 | 110 | 2 | 0 | 0.0 | 0 | 0.0 | 0 | 0.0 |
| 05:35PM | 57 | 73 | 84 | 4427 | 0 | 0 | 0 | 0.0 | 0 | 0.0 | 0 | 0.0 |
| 06:35PM | 37 | 63 | 168 | 3798 | 110 | 2 | 0 | 0.0 | 0 | 0.0 | 0 | 0.0 |
| 07:35PM | 57 | 73 | 84 | 4431 | 0 | 0 | 0 | 0.0 | 0 | 0.0 | 0 | 0.0 |
| 08:35PM | 38 | 63 | 168 | 3797 | 112 | 2 | 0 | 0.0 | 0 | 0.0 | 0 | 0.0 |
| 09:35PM | 57 | 73 | 84 | 4431 | 0 | 0 | 0 | 0.0 | 0 | 0.0 | 0 | 0.0 |
| 10:35PM | 37 | 63 | 170 | 3797 | 112 | 2 | 0 | 0.0 | 0 | 0.0 | 0 | 0.0 |
| 11:35PM | 57 | 74 | 84 | 4432 | 0 | 0 | 0 | 0.0 | 0 | 0.0 | 0 | 0.0 |
| 12:35AM | 37 | 63 | 170 | 3792 | 110 | 2 | 0 | 0.0 | 0 | 0.0 | 0 | 0.0 |
| 01:35AM | 57 | 74 | 84 | 4438 | 0 | 0 | 0 | 0.0 | 0 | 0.0 | 0 | 0.0 |
| 02:35AM | 37 | 62 | 170 | 3784 | 110 | 2 | 0 | 0.0 | 0 | 0.0 | 0 | 0.0 |
| 03:35AM | 57 | 74 | 84 | 4446 | 0 | 0 | 0 | 0.0 | 0 | 0.0 | 0 | 0.0 |
| 04:35AM | 37 | 62 | 170 | 3780 | 112 | 2 | 0 | 0.0 | 0 | 0.0 | 0 | 0.0 |
| 05:35AM | 57 | 74 | 84 | 4449 | 0 | 0 | 0 | 0.0 | 0 | 0.0 | 0 | 0.0 |
| 06:35AM | 37 | 62 | 168 | 3775 | 112 | 2 | 0 | 0.0 | 0 | 0.0 | 0 | 0.0 |
|  | 37 | 68 | 170 | 98575 | 1401 | 31 | 20 | 0.0 | 25 | 0.0 | 16 | 0.0 |

Quinton Q960 Superimposition Scanner
Quik-Summary™ Histogram Report
Patient: Smith, John
Record Date: 11/06/90
Patient ID: 550-78-1234
Analysis Date: 12/03/90
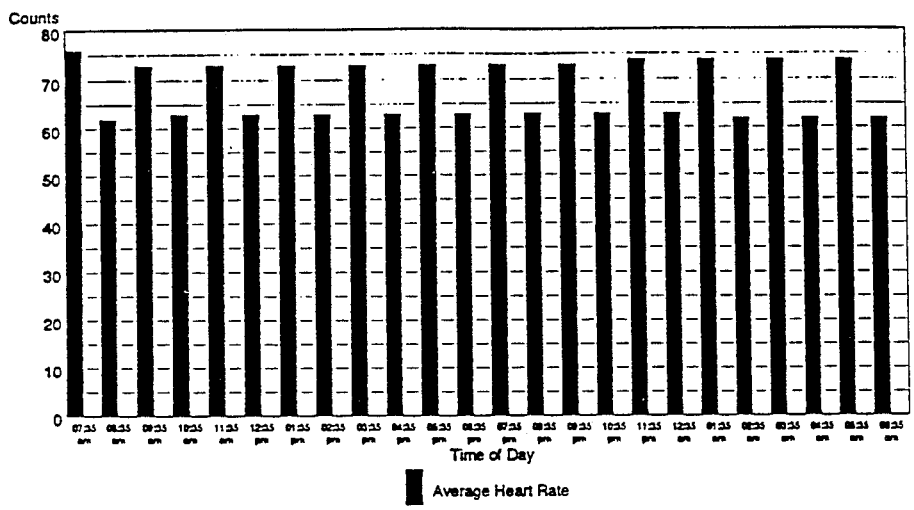
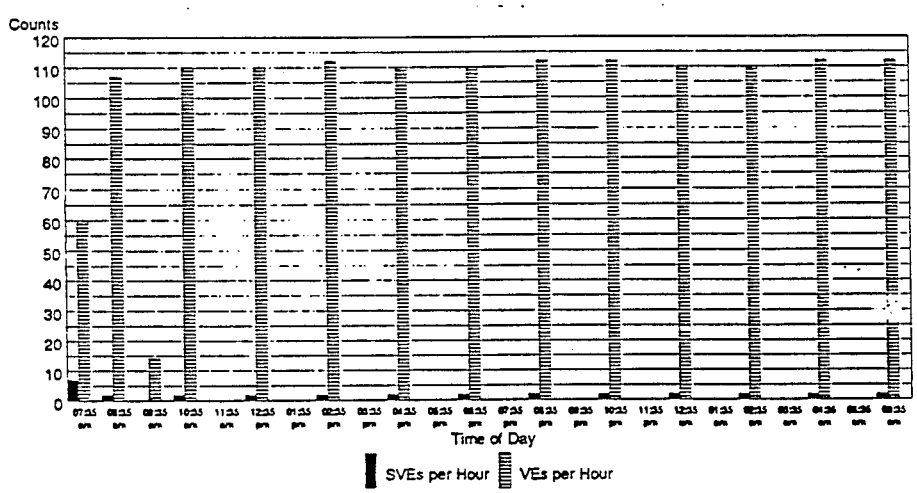

Quinton Q960 Superimposition Scanner
Quik-Summary™ ST Graphs
Patient: Smith, John  
Record Date: 11/06/90
Patient ID: 550-78-1234  
Analysis Date: 12/03/90
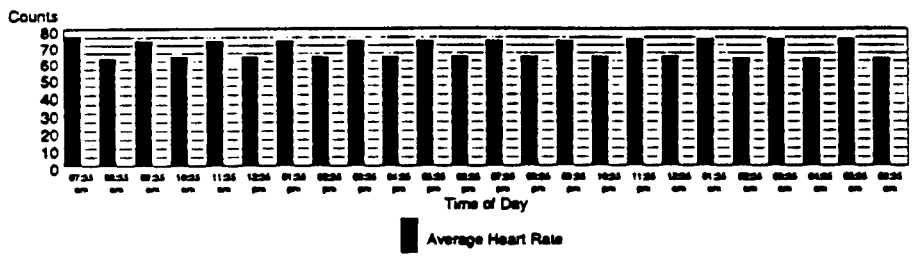
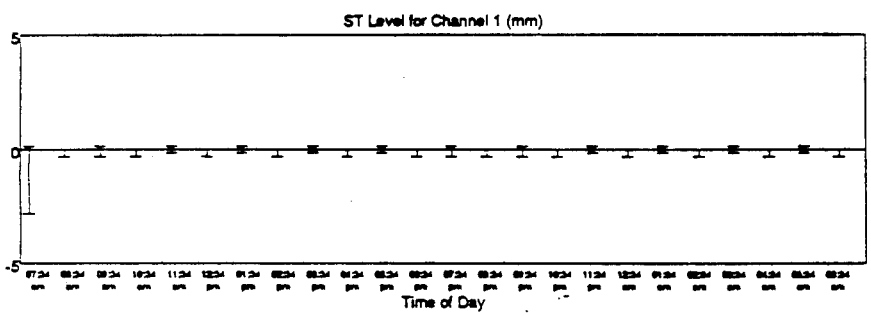
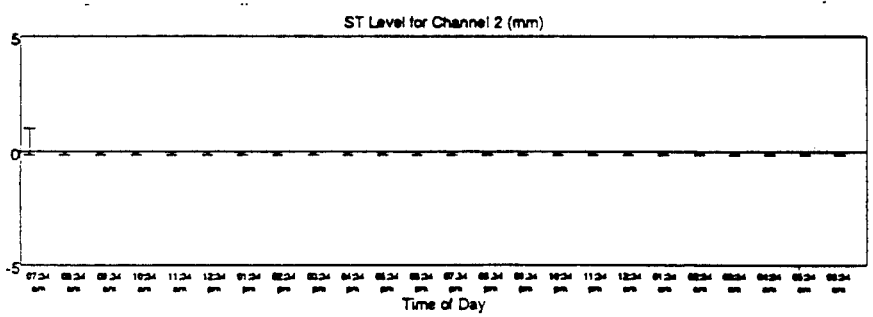
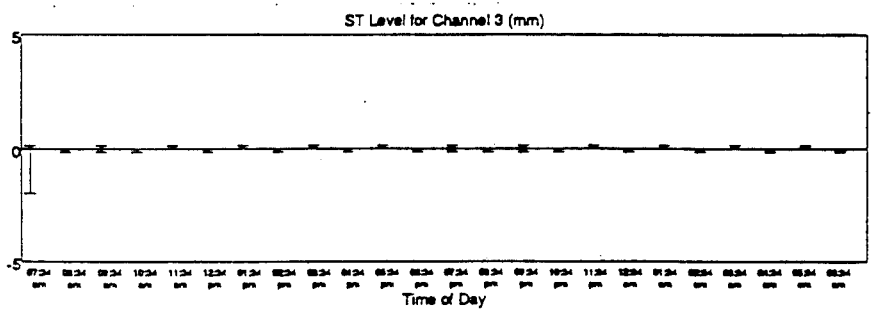

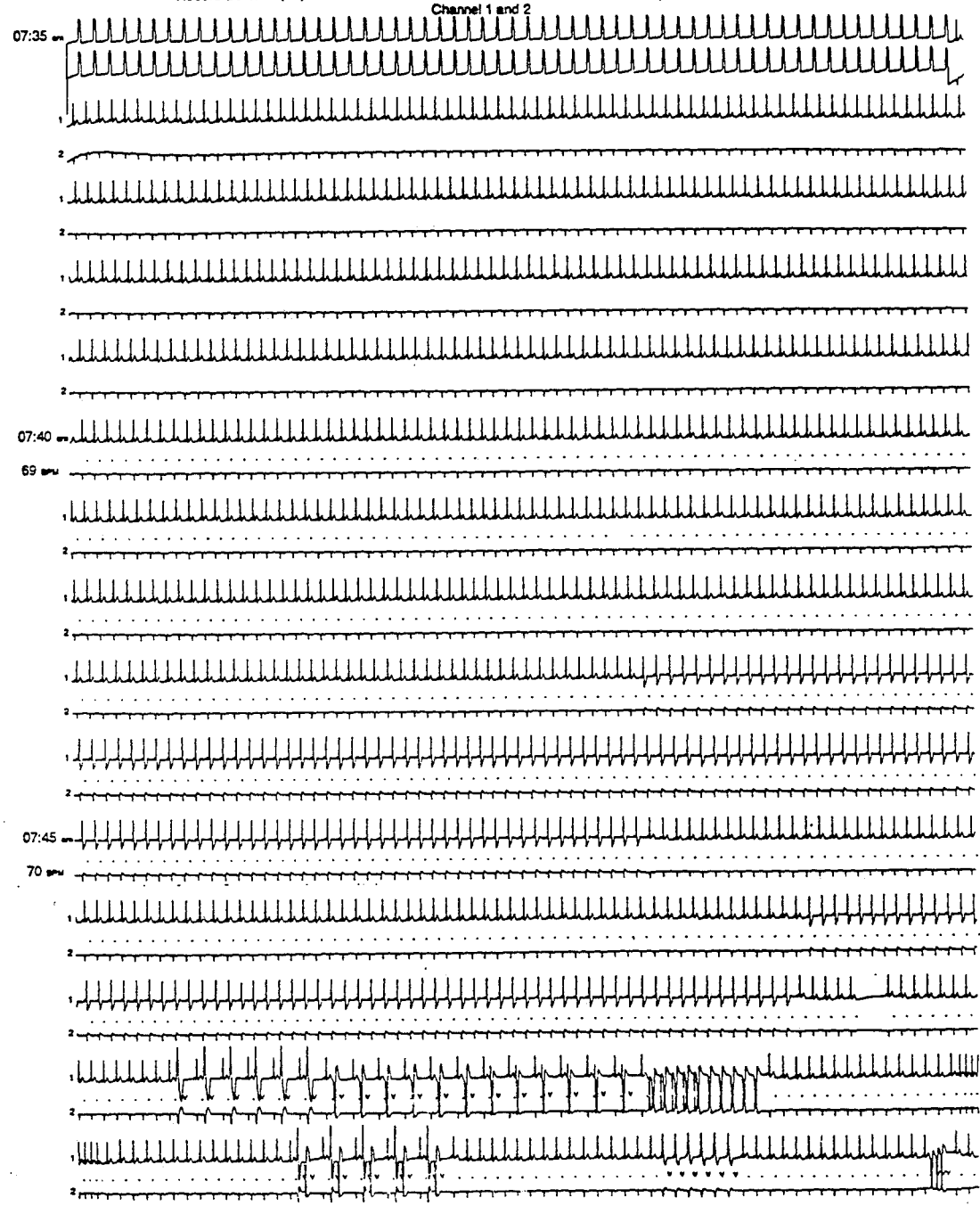

Quinton Q960 Superimposition Scanner
Summary Results

| | | |
|---|---|---|
| SEATTLE CARDIOLOGY CLINIC<br>2121 TERRY AVENUE<br>SEATTLE, WA 98121<br>(206) 223-7373<br>X362-38100 | Patient: Smith, John<br>Address: 1231 Main Street<br>Seattle, WA 98121<br>Telephone: (206) 555-1111<br>Birth date: 10/10/20 | I.D.#: 550-78-1234<br>Record Date: 11/06/90<br>Analysis Date: 12/03/90<br>Referring M.D.: Dr. Blackman, Bellevue, WA<br>Pacemaker: Medtronic   Type: VVI<br>Implant Date: 10/10/89 |
| Hook-up Location: OFFICE<br>Hook-up Tech: DAVE<br>Recorder: Q-CORDER 932, #4<br>Data Quality: Good | Age: 70  Sex: Male  B.P.: 122/078<br>Height: 6'2"  Weight: 190<br>Electrode Placement: CM5, CM1, MCL<br>Analysis Tech: GEORGE | Medicare #: N.A.<br>CPT CODE: 93224 (Q-019)<br>Insurance: CIGNA<br>Policy #: 0256789 |
| Medications: ADVIL, DIGITALIS, LIDOCAINE, NORPACE | Indications: CARDIAC ARRHYTHMIAS, CHEST PAIN / ANGINA, PACEMAKER | Comments: FEELS FINE TODAY. HAD CHEST PAIN YESTERDAY. DID NOT SLEEP WELL. |

```
BASED ON DUAL CHANNEL 24 HOUR AMBULATORY ECG ANALYSIS WITH SUPERIMPOSITION
       SCANNING AND CONTINUOUS FULL DISCLOSURE ECG PRINT-OUT.
```

Record Length 24 Hours  0 Minutes.  Started at 07:35:00 AM

Heart Rate Summary:  Total Beats Detected          98283
    Average: 68  Maximum: 141 @ 07:51 AM  Minimum: 38 @ 09:00 AM
    R-R Interval:  Maximum: 2000 msec @ 08:01 AM  Minimum: 293 msec @ 07:48 AM Ectopic Totals Summary:                                  EVENTS Tachycardia Events (> 120 BPM)           1
        Bradycardia Events (< 40 BPM)            12
        Ventricular Extrasystoles (VES)          1355
        Runs                                     100
        Couplets                                 0
        Bigeminy                                 1
        Trigeminy                                1
        Supraventricular Ectopics (SVE)          29
        Supraventricular Tachycardia (SVT)       1
        Dropped Beats                            77
        Pauses                                   2

Pacemaker Summary:

Total Paced Beats                        20
        Total Not Captured                       25

S-T Summary:

Ch 1:  Ave: 0.0  Min -2.7 @ 07:44 AM  Max 0.0 @ 07:34 AM
    Ch 2:  Ave: 0.0  Min  0.0 @ 07:34 AM  Max 0.8 @ 07:47 AM
    Ch 3:  Ave: 0.0  Min -1.8 @ 07:44 AM  Max 0.0 @ 07:34 AM

Number of Patient Events:                                5

Final Interpretation:_____
_____
_____
_____
_____

Physician Signature:_____  Date:_____
               BARBARA GREEN, M.D.

Quinton Q960 Superimposition Scanner
Hourly Arrhythmia Tabular Report

Patient: Smith, John  
Record Date: 11/06/90  
Patient ID: 550-78-1234  
Analysis Date: 12/03/90

| Hour | Heart Rate Min | Ave | Max | Total QRS | Tachy-cardia | Brady-cardia | VES | Runs | Couplets | Bigem | Trigem | Paced | Non Cap | Fail Sense | Paused | Dropped |
|---|---|---|---|---|---|---|---|---|---|---|---|---|---|---|---|---|
| 07:35AM | 66 | 76 | 141 | 4214 | 1 | 0 | 55 | 4 | 0 | 1 | 1 | 5 | 0 | 10 | 2 | 0 |
| 08:35AM | 38 | 62 | 117 | 3748 | 0 | 1 | 107 | 8 | 0 | 0 | 0 | 0 | 0 | 0 | 0 | 6 |
| 09:35AM | 59 | 73 | 82 | 4402 | 0 | 0 | 6 | 0 | 0 | 0 | 0 | 15 | 24 | 6 | 0 | 0 |
| 10:35AM | 38 | 63 | 127 | 3819 | 0 | 1 | 107 | 8 | 0 | 0 | 0 | 0 | 0 | 0 | 0 | 7 |
| 11:35AM | 59 | 73 | 84 | 4411 | 0 | 0 | 0 | 0 | 0 | 0 | 0 | 0 | 0 | 0 | 0 | 0 |
| 12:35PM | 41 | 63 | 89 | 3813 | 0 | 1 | 107 | 8 | 0 | 0 | 0 | 0 | 0 | 0 | 0 | 6 |
| 01:35PM | 59 | 73 | 83 | 4415 | 0 | 0 | 0 | 0 | 0 | 0 | 0 | 0 | 1 | 0 | 0 | 0 |
| 02:35PM | 39 | 63 | 118 | 3809 | 0 | 1 | 109 | 8 | 0 | 0 | 0 | 0 | 0 | 0 | 0 | 7 |
| 03:35PM | 59 | 73 | 83 | 4419 | 0 | 0 | 0 | 0 | 0 | 0 | 0 | 0 | 0 | 0 | 0 | 1 |
| 04:35PM | 42 | 63 | 108 | 3803 | 0 | 1 | 107 | 8 | 0 | 0 | 0 | 0 | 0 | 0 | 0 | 6 |
| 05:35PM | 59 | 73 | 84 | 4427 | 0 | 0 | 0 | 0 | 0 | 0 | 0 | 0 | 0 | 0 | 0 | 0 |
| 06:35PM | 40 | 63 | 107 | 3798 | 0 | 1 | 107 | 8 | 0 | 0 | 0 | 0 | 0 | 0 | 0 | 6 |
| 07:35PM | 59 | 73 | 82 | 4431 | 0 | 0 | 0 | 0 | 0 | 0 | 0 | 0 | 0 | 0 | 0 | 0 |
| 08:35PM | 39 | 63 | 127 | 3798 | 0 | 1 | 109 | 8 | 0 | 0 | 0 | 0 | 0 | 0 | 0 | 6 |
| 09:35PM | 59 | 73 | 84 | 4431 | 0 | 0 | 0 | 0 | 0 | 0 | 0 | 0 | 0 | 0 | 0 | 0 |
| 10:35PM | 41 | 63 | 89 | 3796 | 0 | 1 | 109 | 8 | 0 | 0 | 0 | 0 | 0 | 0 | 0 | 6 |
| 11:35PM | 59 | 73 | 83 | 4433 | 0 | 0 | 0 | 0 | 0 | 0 | 0 | 0 | 0 | 0 | 0 | 0 |
| 12:35AM | 38 | 63 | 117 | 3791 | 0 | 1 | 107 | 8 | 0 | 0 | 0 | 0 | 0 | 0 | 0 | 7 |
| 01:35AM | 58 | 73 | 83 | 4437 | 0 | 0 | 0 | 0 | 0 | 0 | 0 | 0 | 0 | 0 | 0 | 1 |
| 02:35AM | 43 | 63 | 108 | 3784 | 0 | 1 | 107 | 8 | 0 | 0 | 0 | 0 | 0 | 0 | 0 | 6 |
| 03:35AM | 61 | 74 | 84 | 4445 | 0 | 0 | 0 | 0 | 0 | 0 | 0 | 0 | 0 | 0 | 0 | 0 |
| 04:35AM | 40 | 63 | 108 | 3780 | 0 | 1 | 109 | 8 | 0 | 0 | 0 | 0 | 0 | 0 | 0 | 6 |
| 05:35AM | 59 | 74 | 82 | 4449 | 0 | 0 | 0 | 0 | 0 | 0 | 0 | 0 | 0 | 0 | 0 | 0 |
| 06:35AM | 38 | 63 | 128 | 3630 | 0 | 1 | 109 | 8 | 0 | 0 | 0 | 0 | 0 | 0 | 0 | 6 |
| Totals | 38 | 68 | 141 | 98283 | 1 | 12 | 1355 | 100 | 0 | 1 | 1 | 20 | 25 | 16 | 2 | 77 |

Quinton Q960 Superimposition Scanner
Hourly Arrhythmia Tabular Report

Patient: Smith, John  
Record Date: 11/06/90  
Patient ID: 550-78-1234  
Analysis Date: 12/03/90

| Hour | Heart Rate Min | Ave | Max | Total QRS | Total SVE | Total SVT | ST Level Ch 1 min | ave | max | ST Level Ch 2 min | ave | max | ST Level Ch 3 min | ave | max |
|---|---|---|---|---|---|---|---|---|---|---|---|---|---|---|---|
| 07:35AM | 66 | 76 | 141 | 4214 | 7 | 1 | -2.7 | 0.0 | 0.0 | 0.0 | 0.0 | 0.8 | -1.8 | 0.0 | 0.0 |
| 08:35AM | 38 | 62 | 117 | 3748 | 2 | 0 | -0.2 | 0.0 | 0.0 | 0.0 | 0.0 | 0.0 | -0.2 | 0.0 | 0.0 |
| 09:35AM | 59 | 73 | 82 | 4402 | 0 | 0 | 0.0 | 0.0 | 0.0 | 0.0 | 0.0 | 0.0 | 0.0 | 0.0 | 0.0 |
| 10:35AM | 38 | 63 | 127 | 3819 | 3 | 0 | -0.2 | 0.0 | 0.0 | 0.0 | 0.0 | 0.0 | 0.0 | 0.0 | 0.0 |
| 11:35AM | 59 | 73 | 84 | 4411 | 0 | 0 | 0.0 | 0.0 | 0.0 | 0.0 | 0.0 | 0.0 | 0.0 | 0.0 | 0.0 |
| 12:35PM | 41 | 63 | 89 | 3813 | 2 | 0 | -0.2 | 0.0 | 0.0 | 0.0 | 0.0 | 0.0 | 0.0 | 0.0 | 0.0 |
| 01:35PM | 59 | 73 | 83 | 4415 | 0 | 0 | 0.0 | 0.0 | 0.0 | 0.0 | 0.0 | 0.0 | 0.0 | 0.0 | 0.0 |
| 02:35PM | 39 | 63 | 118 | 3809 | 2 | 0 | 0.0 | 0.0 | 0.0 | 0.0 | 0.0 | 0.0 | 0.0 | 0.0 | 0.0 |
| 03:35PM | 59 | 73 | 83 | 4419 | 0 | 0 | -0.2 | 0.0 | 0.0 | 0.0 | 0.0 | 0.0 | 0.0 | 0.0 | 0.0 |
| 04:35PM | 42 | 63 | 108 | 3803 | 1 | 0 | 0.0 | 0.0 | 0.0 | 0.0 | 0.0 | 0.0 | 0.0 | 0.0 | 0.0 |
| 05:35PM | 59 | 73 | 84 | 4427 | 0 | 0 | -0.2 | 0.0 | 0.0 | 0.0 | 0.0 | 0.0 | 0.0 | 0.0 | 0.0 |
| 06:35PM | 40 | 63 | 107 | 3798 | 1 | 0 | 0.0 | 0.0 | 0.0 | 0.0 | 0.0 | 0.0 | 0.0 | 0.0 | 0.0 |
| 07:35PM | 59 | 73 | 82 | 4431 | 0 | 0 | -0.2 | 0.0 | 0.0 | 0.0 | 0.0 | 0.0 | 0.0 | 0.0 | 0.0 |
| 08:35PM | 39 | 63 | 127 | 3798 | 2 | 0 | 0.0 | 0.0 | 0.0 | 0.0 | 0.0 | 0.0 | 0.0 | 0.0 | 0.0 |
| 09:35PM | 59 | 73 | 84 | 4431 | 0 | 0 | 0.0 | 0.0 | 0.0 | 0.0 | 0.0 | 0.0 | 0.0 | 0.0 | 0.0 |
| 10:35PM | 41 | 63 | 89 | 3796 | 2 | 0 | -0.2 | 0.0 | 0.0 | 0.0 | 0.0 | 0.0 | -0.2 | 0.0 | 0.0 |
| 11:35PM | 59 | 73 | 83 | 4433 | 0 | 0 | 0.0 | 0.0 | 0.0 | 0.0 | 0.0 | 0.0 | 0.0 | 0.0 | 0.0 |
| 12:35AM | 38 | 63 | 117 | 3791 | 2 | 0 | -0.2 | 0.0 | 0.0 | 0.0 | 0.0 | 0.0 | 0.0 | 0.0 | 0.0 |
| 01:35AM | 58 | 73 | 83 | 4437 | 0 | 0 | 0.0 | 0.0 | 0.0 | 0.0 | 0.0 | 0.0 | 0.0 | 0.0 | 0.0 |
| 02:35AM | 43 | 63 | 108 | 3784 | 1 | 0 | -0.2 | 0.0 | 0.0 | 0.0 | 0.0 | 0.0 | 0.0 | 0.0 | 0.0 |
| 03:35AM | 61 | 74 | 84 | 4445 | 0 | 0 | 0.0 | 0.0 | 0.0 | 0.0 | 0.0 | 0.0 | 0.0 | 0.0 | 0.0 |
| 04:35AM | 40 | 63 | 108 | 3780 | 2 | 0 | -0.2 | 0.0 | 0.0 | 0.0 | 0.0 | 0.0 | 0.0 | 0.0 | 0.0 |
| 05:35AM | 59 | 74 | 82 | 4449 | 0 | 0 | 0.0 | 0.0 | 0.0 | 0.0 | 0.0 | 0.0 | 0.0 | 0.0 | 0.0 |
| 06:35AM | 38 | 63 | 128 | 3630 | 2 | 0 | -2.7 | 0.0 | 0.0 | 0.0 | 0.0 | 0.8 | -1.8 | 0.0 | 0.0 |
| Totals | 38 | 68 | 141 | 98283 | 29 | 1 | -2.7 | 0.0 | 0.0 | 0.0 | 0.0 | 0.8 | -1.8 | 0.0 | 0.0 |

Quinton Q960 Superimposition Scanner
ST Trend Summary
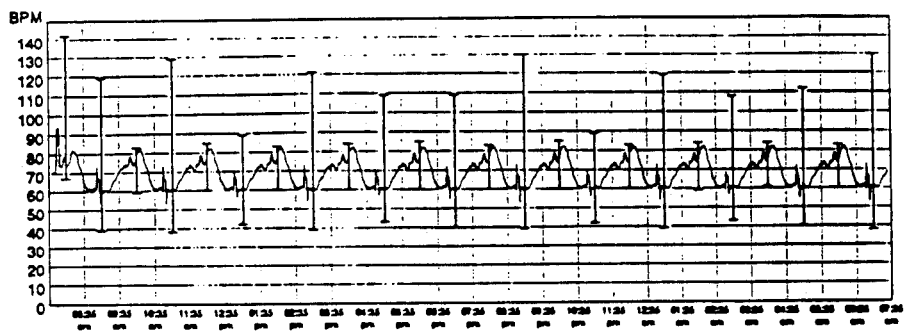
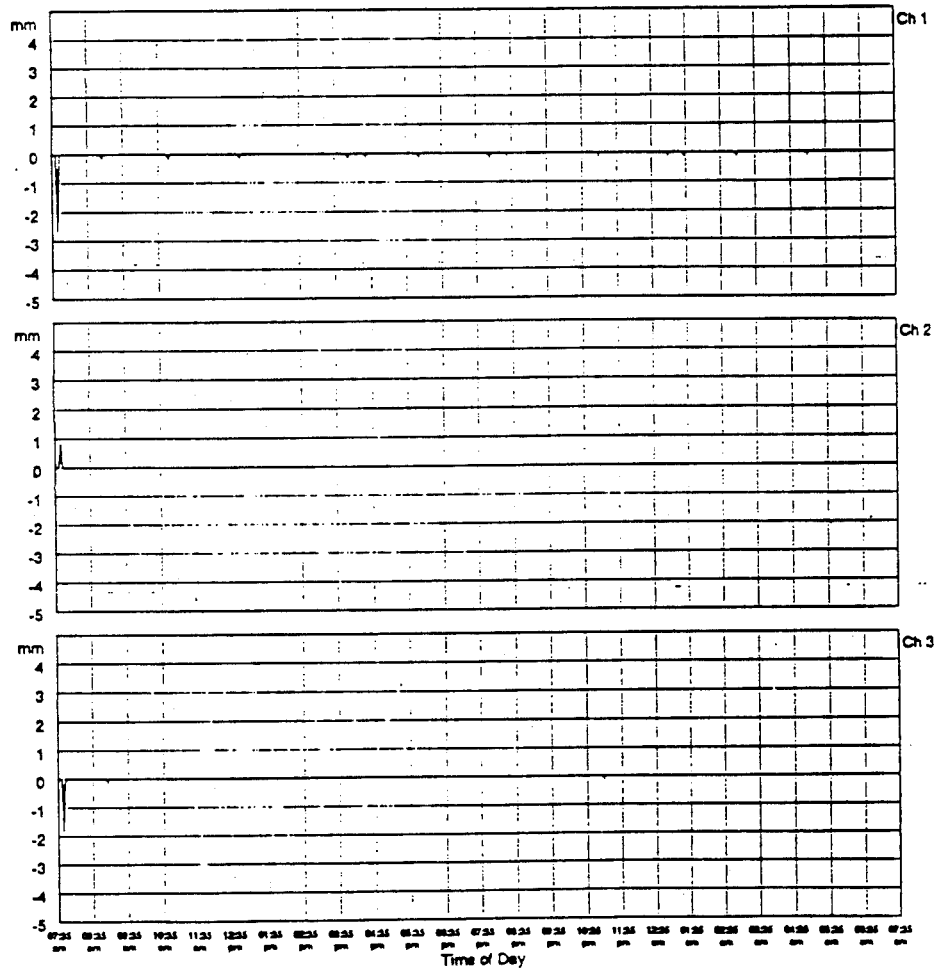
Time of Day
Quinton Q960 Superimposition Scanner
Patient Event Summary
Patient: Smith, John  
Record Date: 11/06/90  
Patient ID: 550-78-1234  
Analysis Date: 12/03/90
| Time | Heart Rate | Tachy | Brady | VES | Runs | Couplets | Bigem | Trigem | Paced | Ch 1 | Ch 2 | Ch 3 |
|---|---|---|---|---|---|---|---|---|---|---|---|---|
| 7:43 am | 70 | 0 | 0 | 0 | 0 | 0 | 0 | 0 | 0 | -1.00 | 0.33 | -0.50 |
| 7:45 am | 70 | 0 | 0 | 0 | 0 | 0 | 0 | 0 | 0 | -1.83 | 0.50 | -1.16 |
| 7:47 am | 67 | 0 | 0 | 0 | 0 | 0 | 0 | 0 | 0 | -2.32 | 0.83 | -1.49 |
| 7:50 am | 104 | 1 | 0 | 13 | 2 | 0 | 0 | 0 | 0 | 0.00 | 0.00 | 0.00 |
| 9:44 am | 70 | 0 | 0 | 0 | 0 | 0 | 0 | 0 | 0 | 0.00 | 0.00 | 0.00 |

Quinton Q960 Superimposition Scanner
Patient Diary

Patient: Smith, John
Record Date: 11/06/90

Patient ID: 550-78-1234
Analysis Date: 12/03/90

| Time | Patient Comments | Physician Comments |
|---|---|---|
| 7:35 AM | Leave doctor's office. Feel fine. | |
| 7:45 AM | Drive to work. Chest pain. | |
| 11:45 AM | Walk to lunch. Feel fine. | |
| 12:45 PM | Walk to work. Dizzy. | |
| 5:00 PM | Drive home. Chest pain. | |
| 7:00 PM | Eat dinner. Feel fine. | |
| 11:00 PM | Go to sleep. Dizzy. | |
| 6:00 AM | Wake up. Go to bathroom. | |

Quinton Q960 Superimposition Scanner
Histogram of R-R Intervals

Patient: Smith, John
Record Date: 11/06/90

Patient ID: 550-78-1234
Analysis Date: 12/03/90

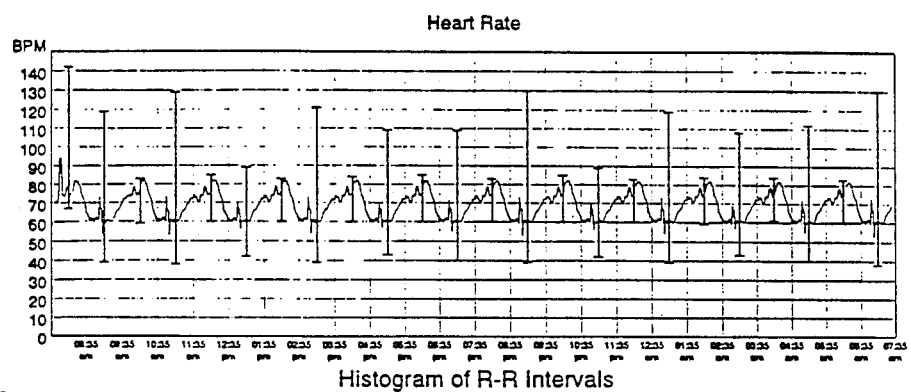

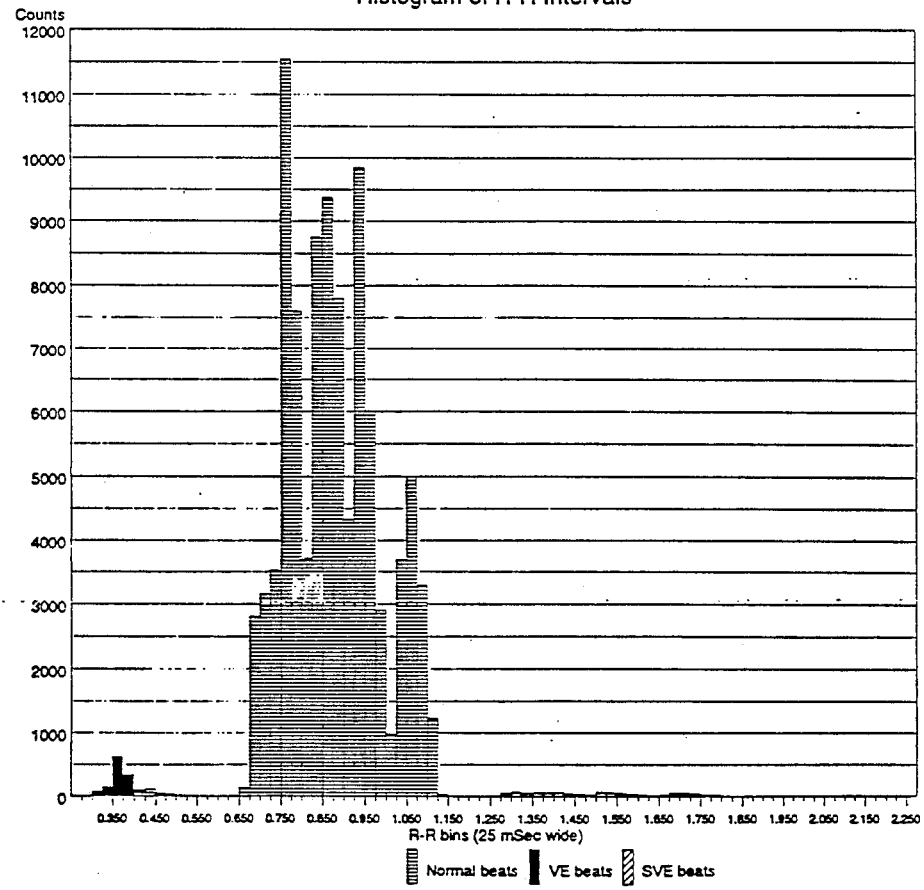

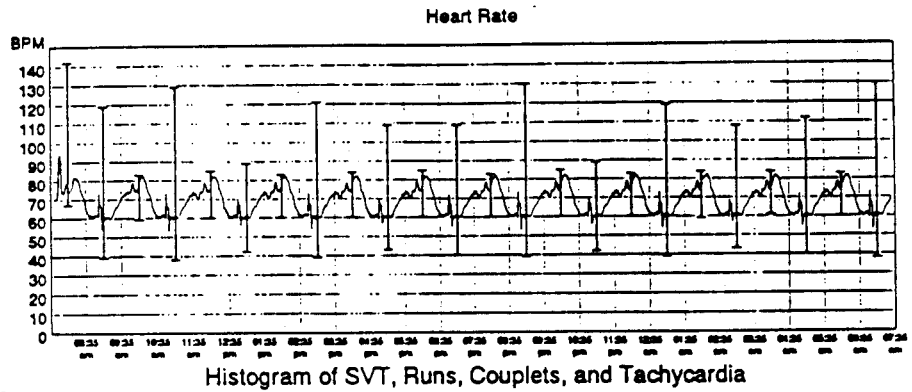
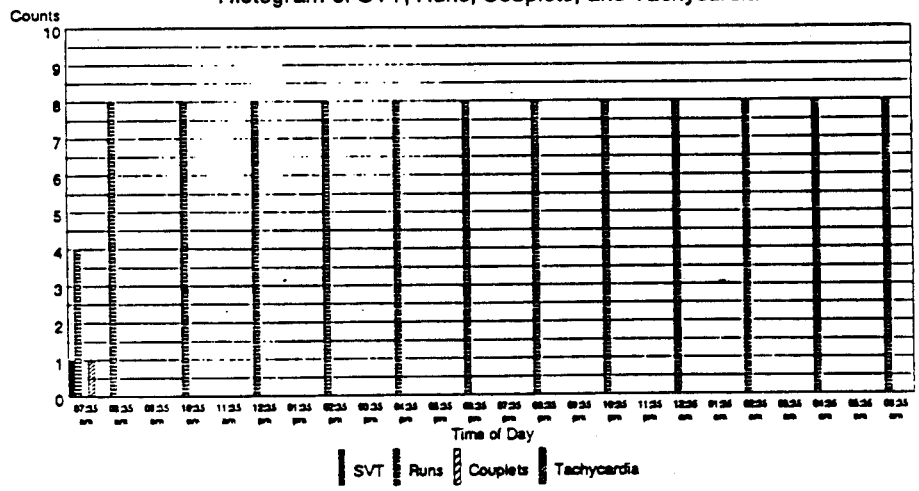
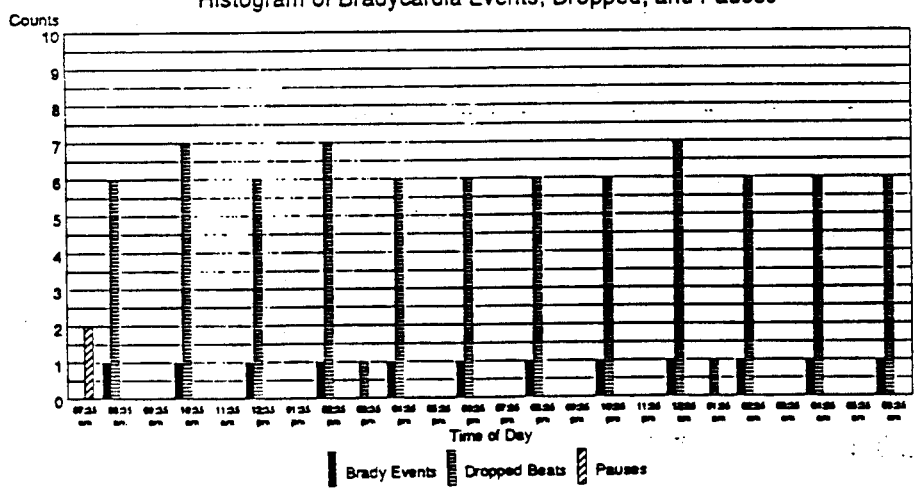

Quinton Q960 Superimposition Scanner
Patient: Smith, John
Record Date: 11/06/90
Patient ID: 550-78-1234
Analysis Date: 12/03/90
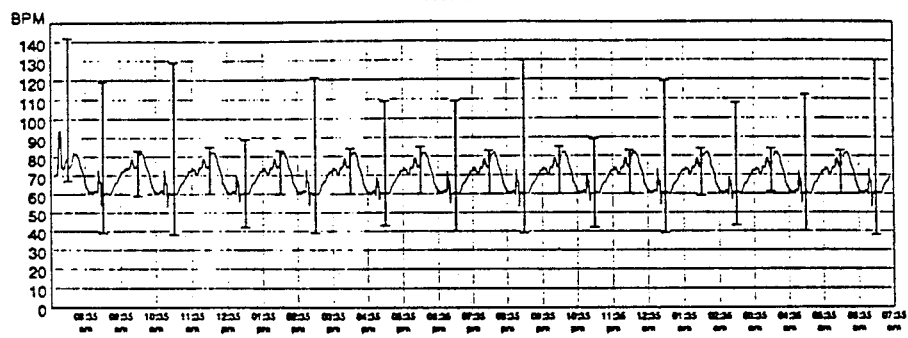
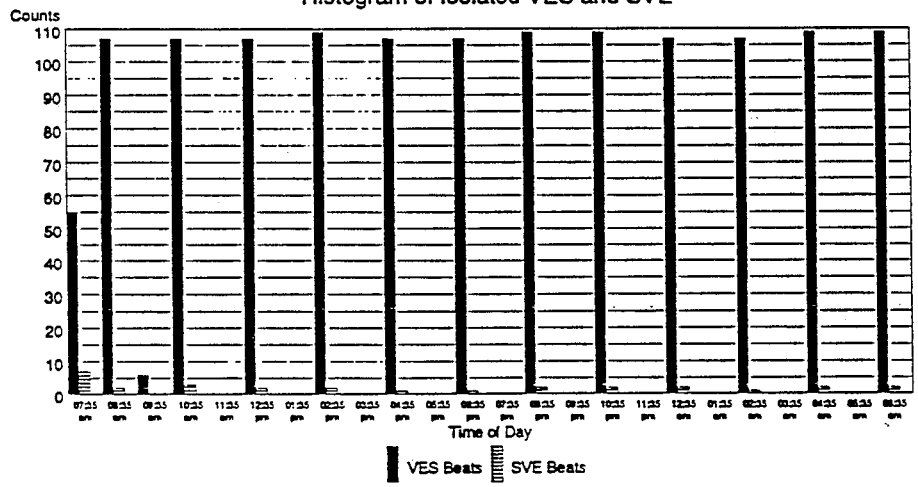
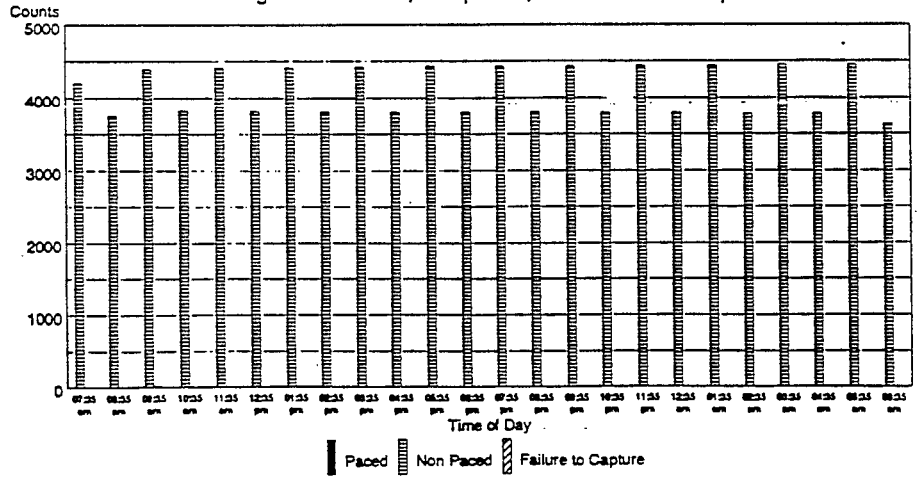

Quinton Q960 Superimposition Scanner
Patient: Smith, John
Record Date: 11/06/90
Patient ID: 550-78-1234
Analysis Date: 12/03/90
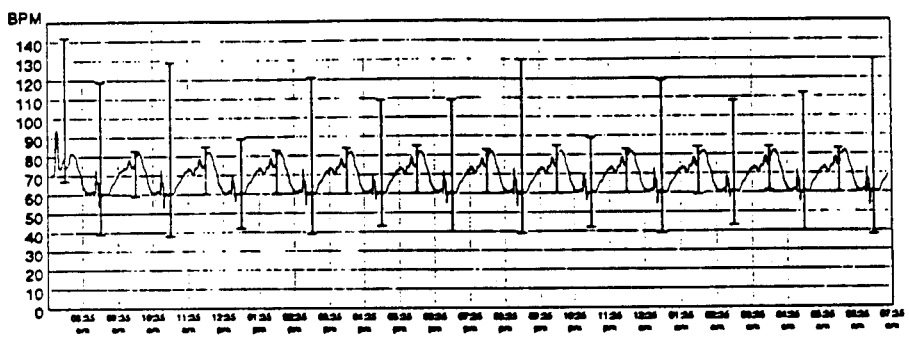
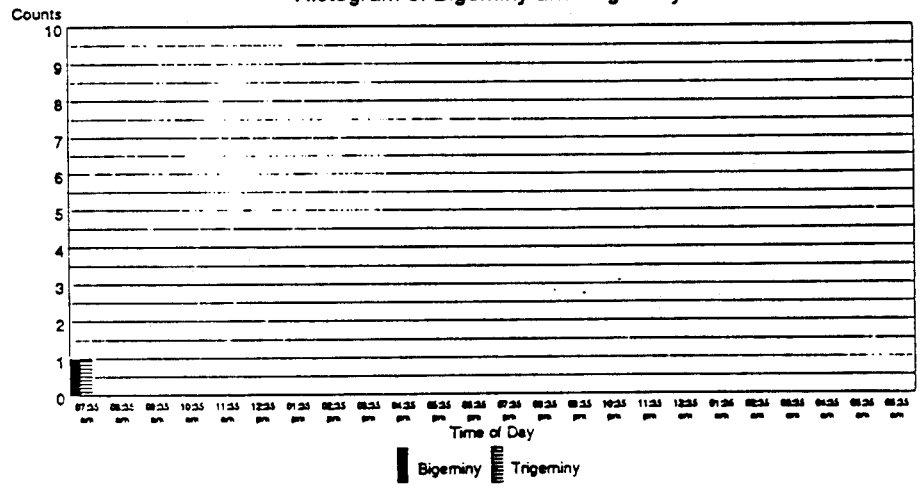
Quinton Q960 Superimposition Scanner
Isolated Morphology Samples
Patient: Smith, John
Record Date: 11/06/90
Patient ID: 550-78-1234
Analysis Date: 12/03/90
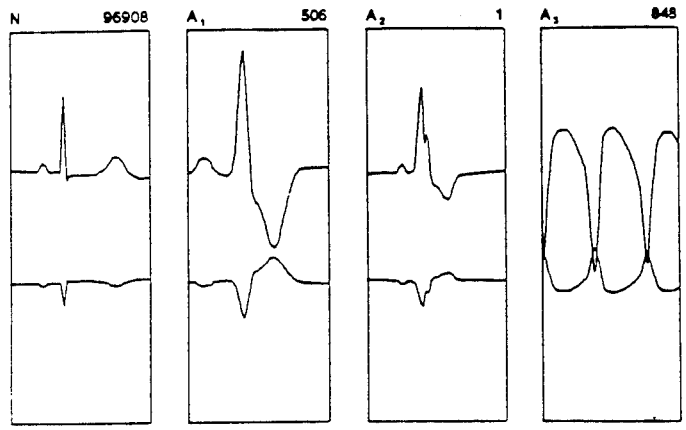

Quinton Q960 Superimposition Scanner
User Selected ECG Strips
Patient: Smith, John
Record Date: 11/06/90
Gain: Channel 1 = 1.0, Channel 2 = 1.0
Patient ID: 550-78-1234
Analysis Date: 12/03/90
07:35:38 am
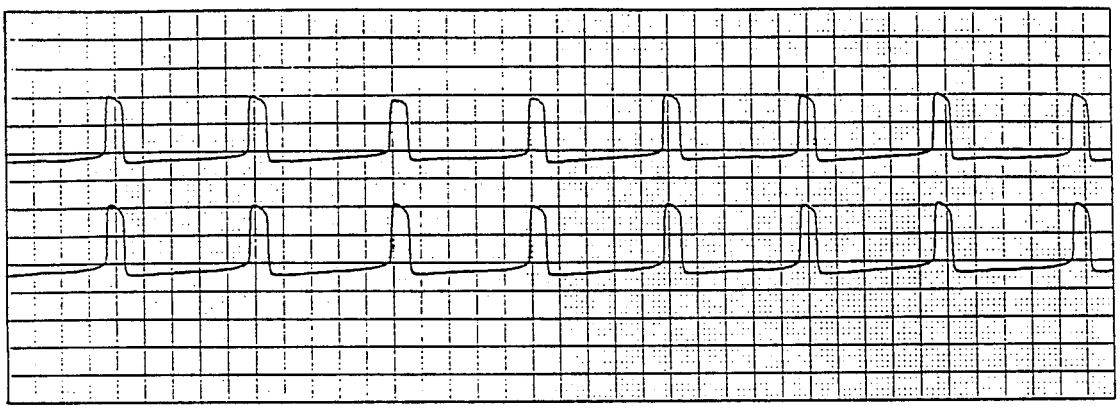
07:38:17 am
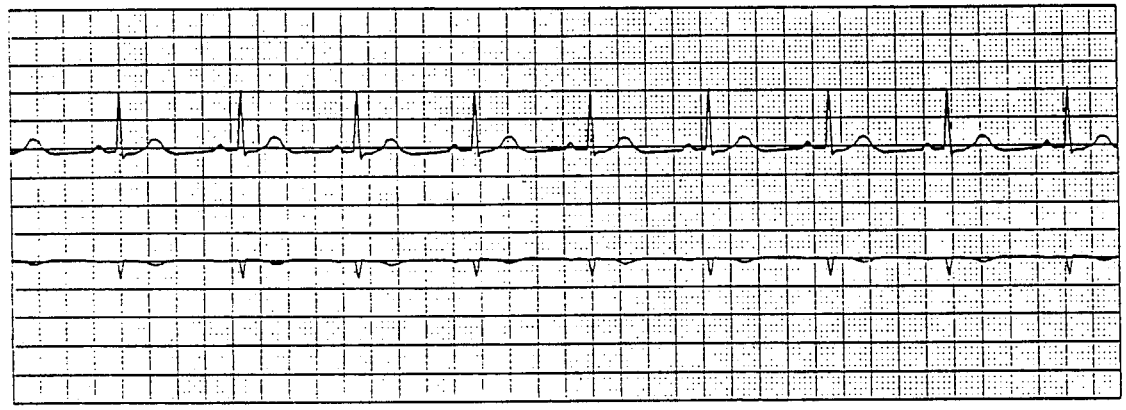
07:48:04 am 72 BPM
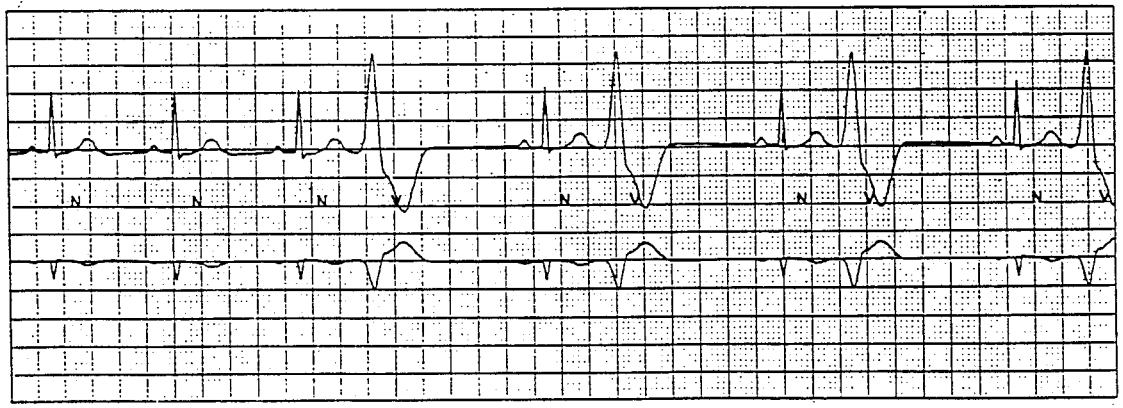

Quinton Q960 Superimposition Scanner
User Selected ECG Strips
Patient: Smith, John  
Record Date: 11/06/90  
Patient ID: 550-78-1234  
Analysis Date: 12/03/90  
Gain: Channel 1 = 1.0, Channel 2 = 1.0
07:48:17 — 69 BPM
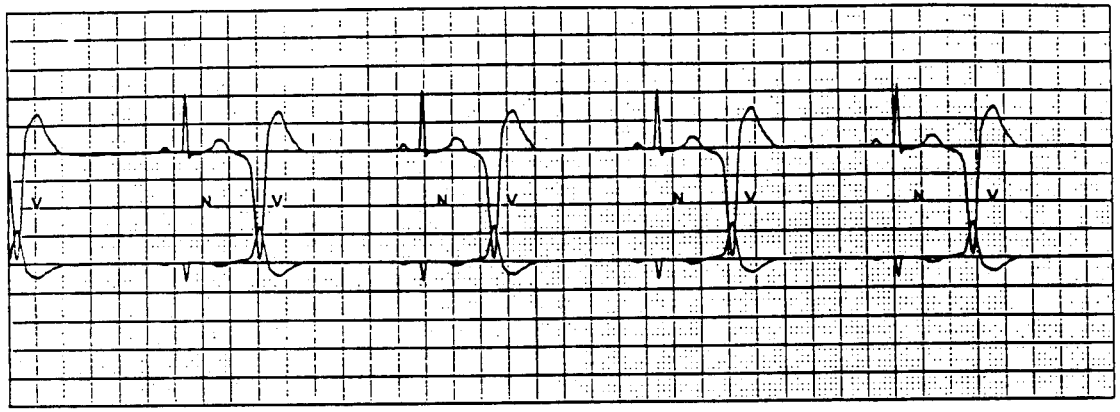
07:48:36 — 75 BPM
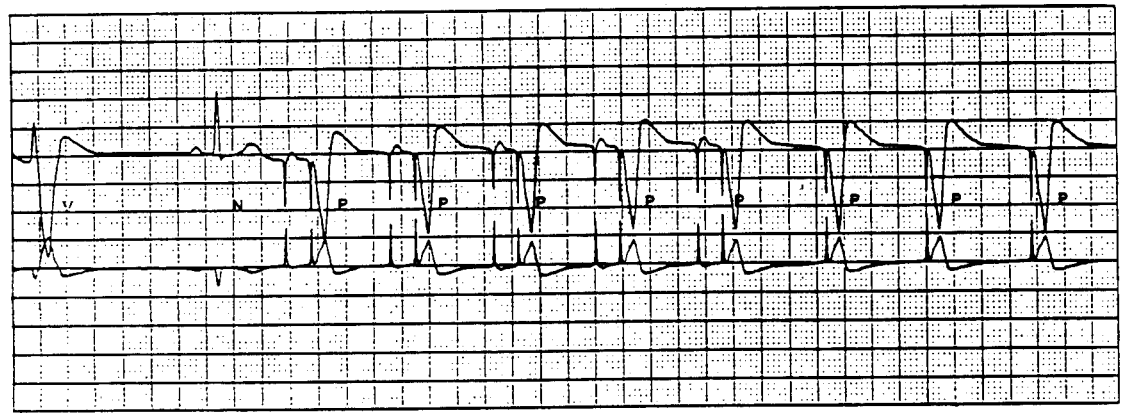
07:48:56 — 99 BPM
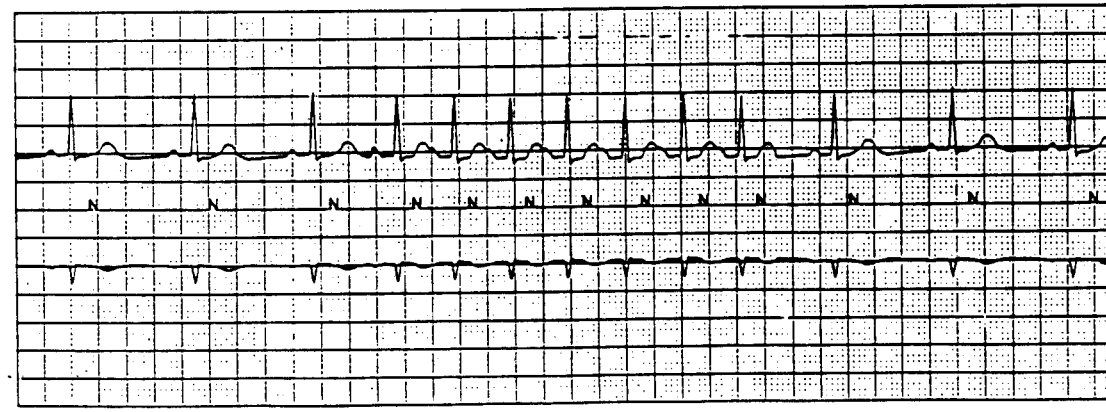

Quinton Q960 Superimposition Scanner
User Selected ECG Strips
Patient: Smith, John  
Record Date: 11/06/90  
Patient ID: 550-78-1234  
Analysis Date: 12/03/90  
Gain: Channel 1 = 1.0, Channel 2 = 1.0
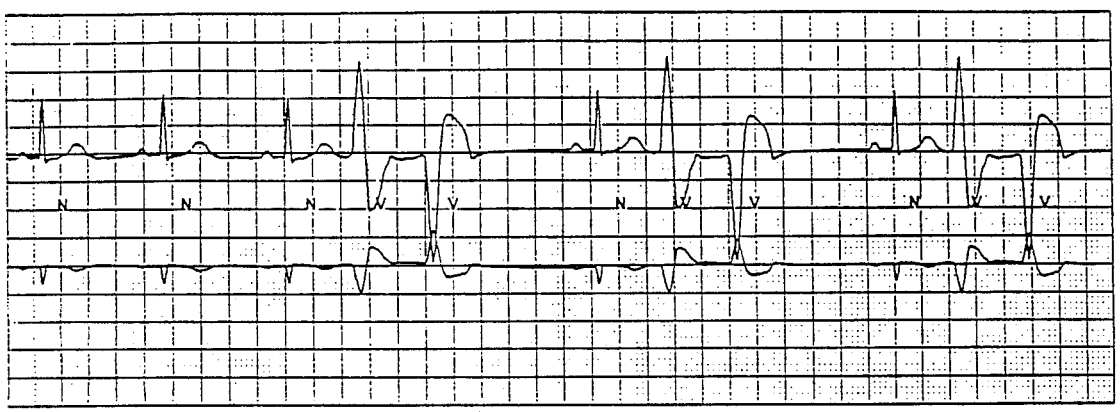
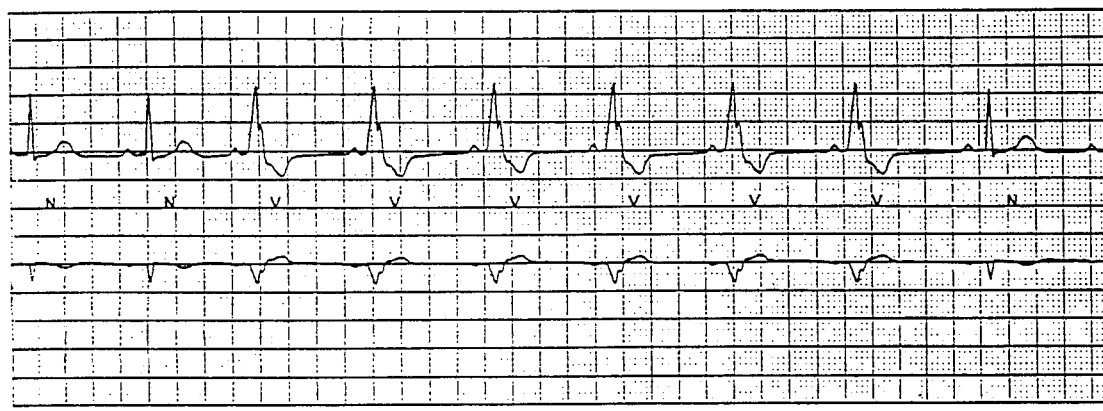
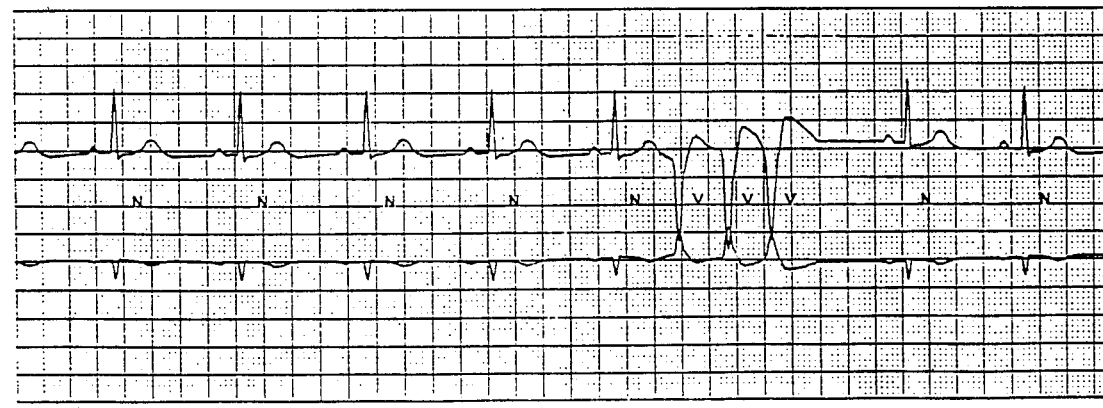

Qu...on Q960 Superimposition Scanner
Arrhythmia Sample ECG Strips
Patient: Smith, John  
Record Date: 11/06/90  
Gain: Channel 1 = 1.0, Channel 2 = 1.0  
Patient ID: 550-78-1234  
Analysis Date: 12/03/90
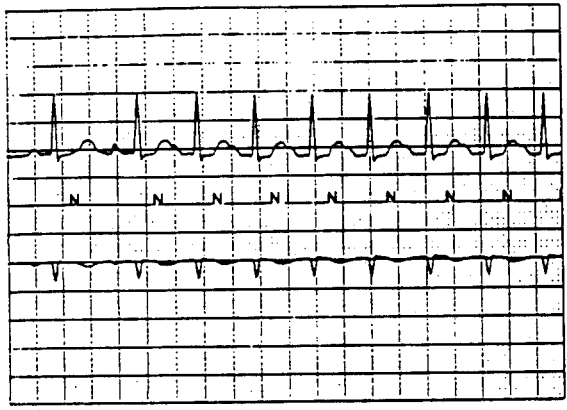
07:50:36 — 137 BPM Highest Tachycardia
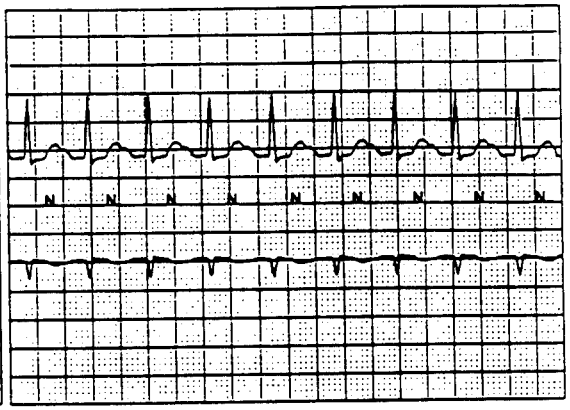
07:52:00 — 135 BPM Highest Tachycardia
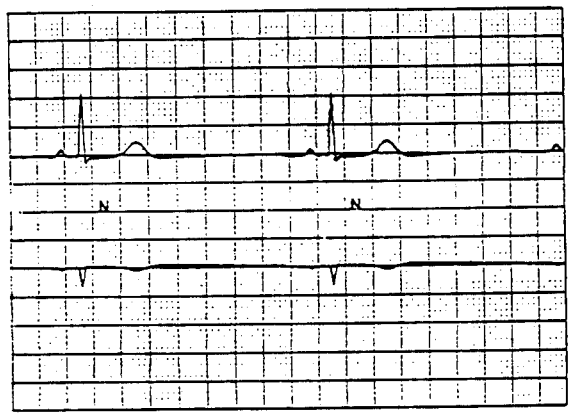
08:59:59 — 30 BPM Lowest Bradycardia
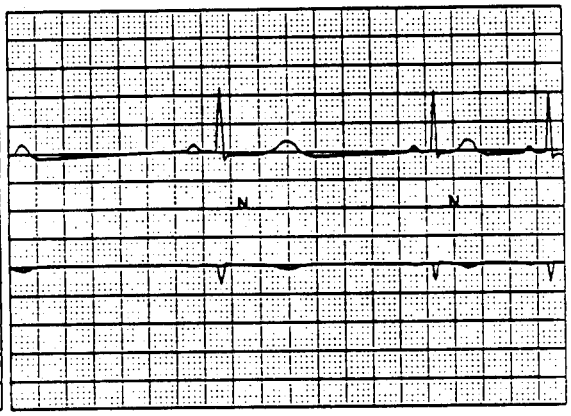
09:01:39 — 50 BPM Lowest Bradycardia
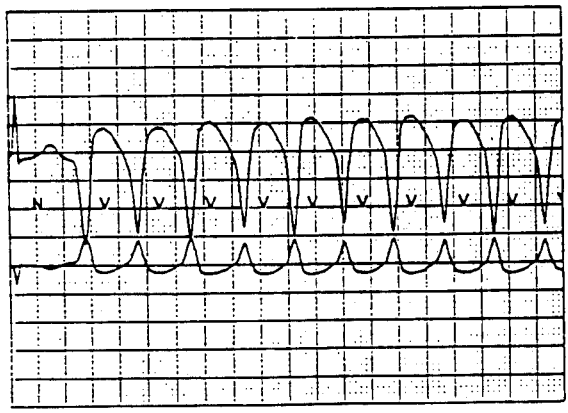
06:55:28 — 158 BPM Longest Run
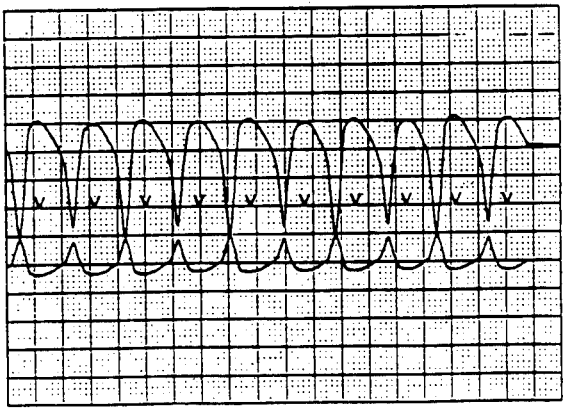
06:55:57 — 161 BPM Longest Run Quinton Q960 Superimposition Scanner
Arrhythmia Sample ECG Strips
Patient: Smith, John
Record Date: 11/06/90
Patient ID: 550-78-1234
Analysis Date: 12/03/90
Gain: Channel 1 = 1.0, Channel 2 = 1.0
07:48:58 am 128 BPM 1st SVT
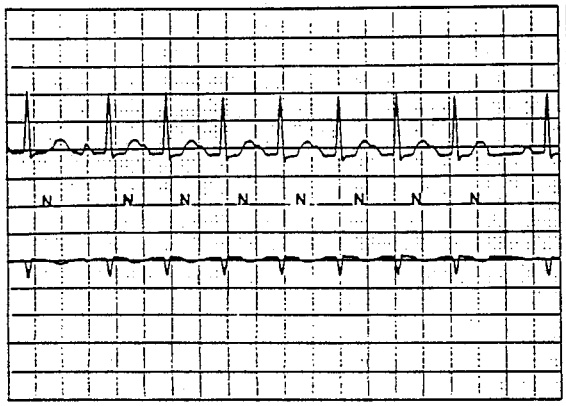
07:48:58 am 128 BPM Highest SVT
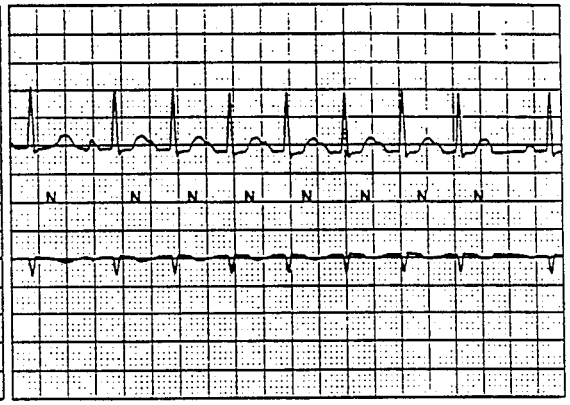
07:48:05 am 75 BPM Longest BI
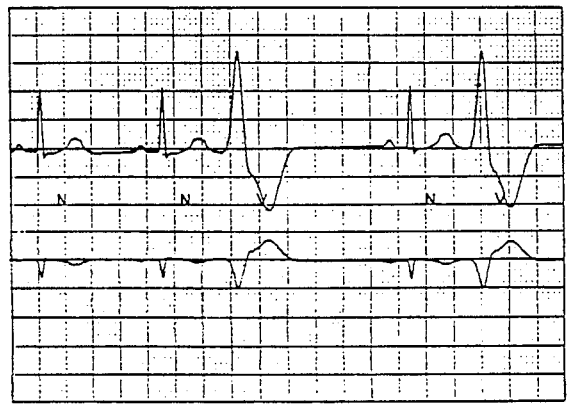
07:48:33 am 76 BPM Longest BI
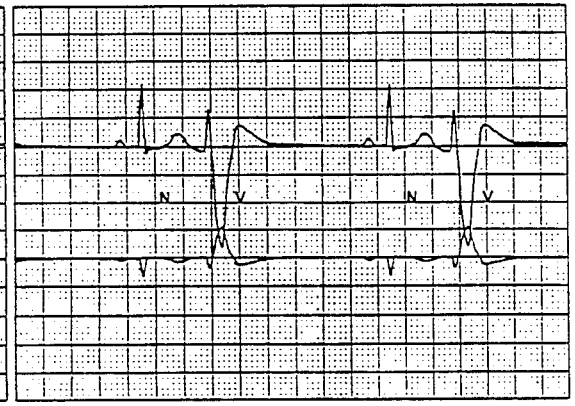
08:59:47 am 98 BPM 1st Dropped
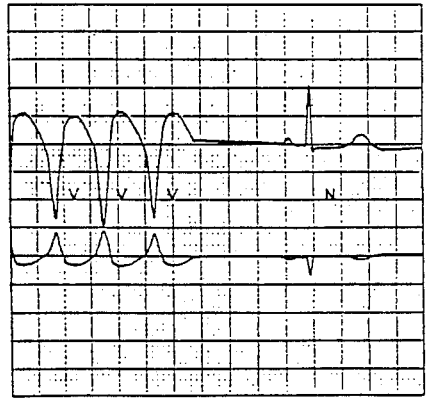
07:47:50 am 35 BPM Longest Pause
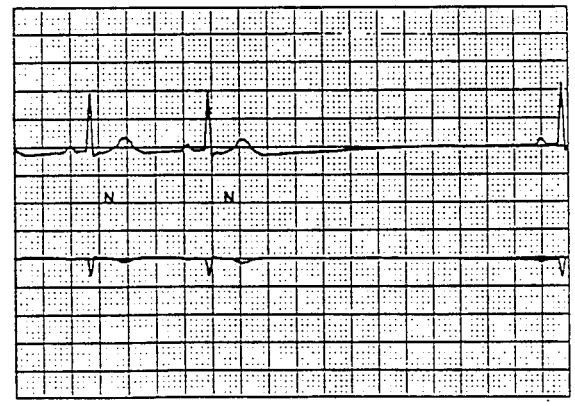

Quinton Q960 Superimposition Scanner
ST Levels
Patient: Smith, John
Record Date: 11/06/90
Patient ID: 550-78-1234
Analysis Date: 12/03/90
07:43:26 — 70 BPM First ST Depression
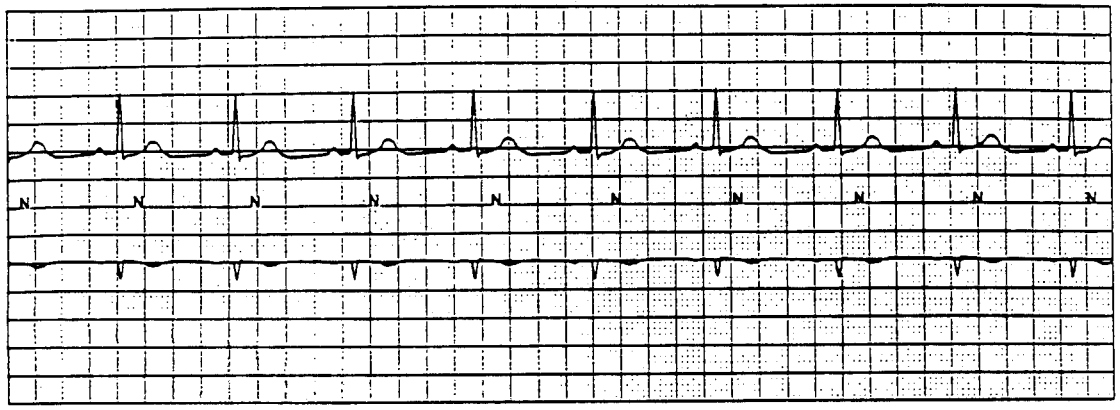
07:45:26 — 70 BPM Longest ST Depression
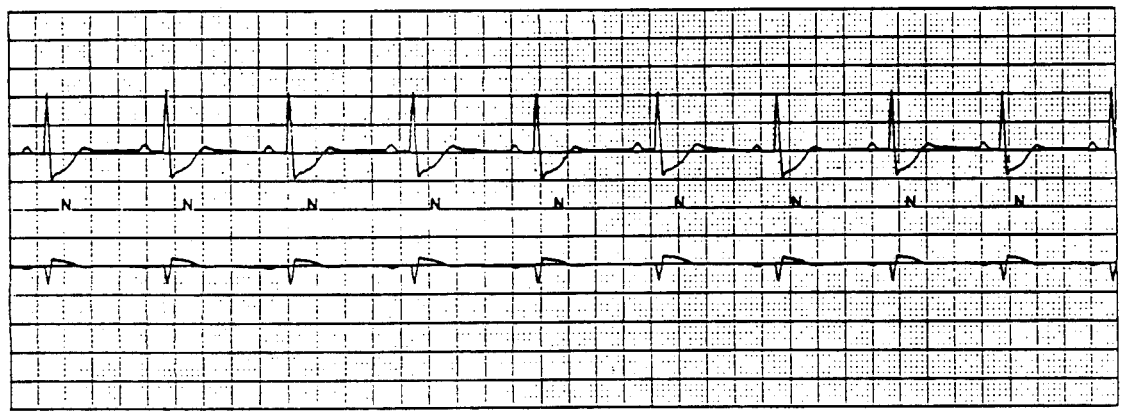

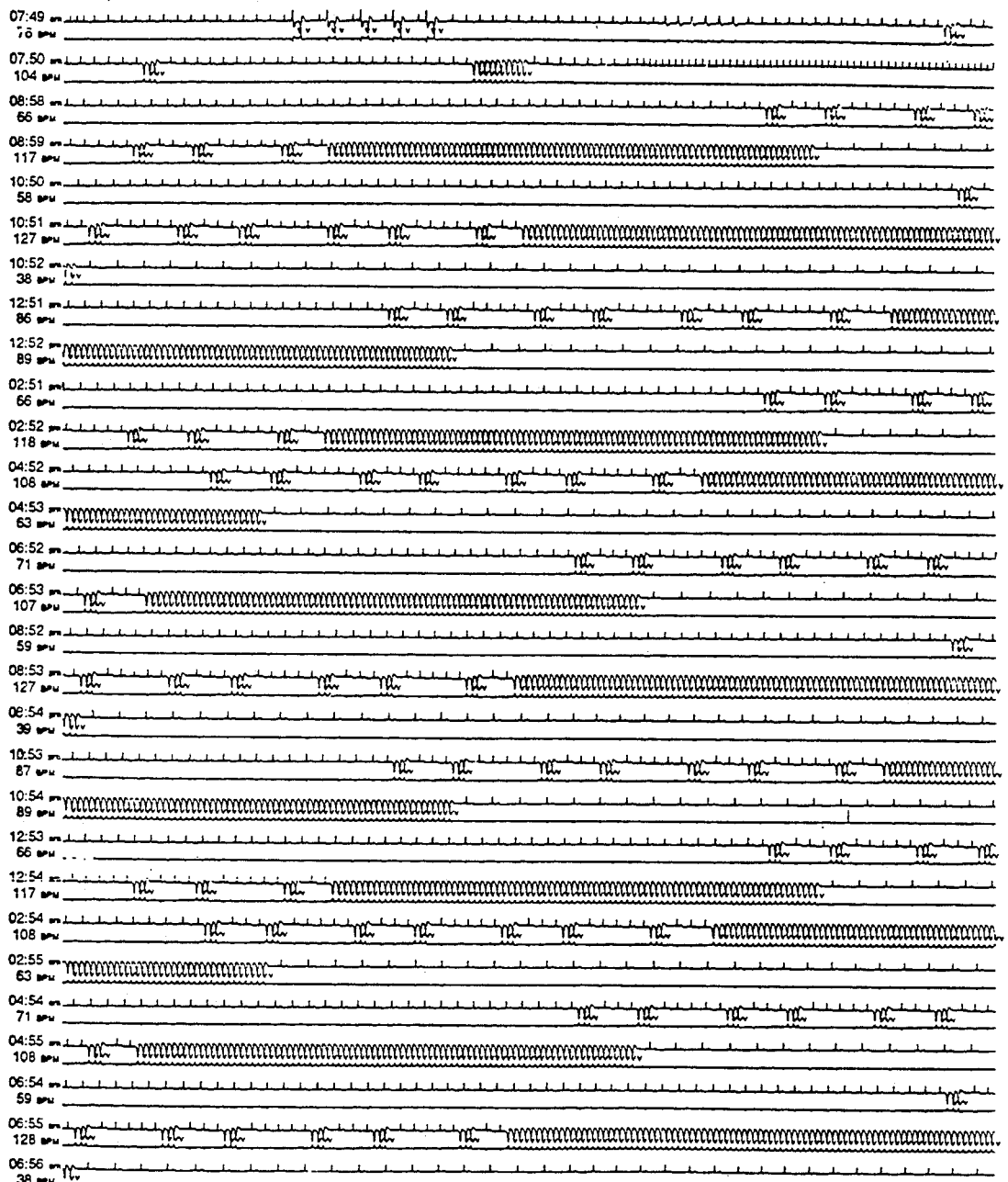

Quinton Q960 Superimposition Scanner
Full Disclosure Arrhythmia Report

What is claimed is:

1. An ambulatory ECG monitoring system comprising:

playback means for downloading ECG data from a data storage medium, said playback means including an analog circuit board means, a digital circuit board means including a microprocessor, and a data storage medium interface means, said analog circuit board means, said digital circuit board means and said data storage medium interface means being operatively associated with each other and positioned in structurally cooperative relationship with each other within said playback means.

processor means for analysis, manipulation, and editing of data received from said playback means, and playback/processor linking means for linking said playback means and said processor means for transfer of information between said playback means and said processor means, whereby said digital circuit board means said analog circuit board means are electrically isolated from each other to prevent operation of said digital circuit board means from causing electrical interface with data manipulation operations of said analog circuit board means.

2. A system according to claim 1 wherein said analog circuit board means and said digital circuit board means comprise printed circuit boards.

3. A system according to claim 1 wherein said data storage medium is a cassette tape and said data storage medium interface means of said playback means includes a tape transport mechanism.

4. A system according to claim 1 wherein said microprocessor of said playback means receives and interprets operational commands from said processor means, and operates to control said analog circuit board means and said tape transport mechanism according to said operational commands.

5. A system according to claim 1 wherein
said processor means includes means for generating at least one template means for correlating ECG data and facilitating user interaction with said processor means.

6. A system according to claim 5 further including monitor means operatively associated with said playback means for displaying said at least one template means.

7. A system according to claim 6 wherein said at least one template means includes means for displaying an eight second section of analog ECG heart beat waveform data in superimposition.

8. A system according to claim 7 wherein said means for displaying a superimposition of eight seconds of ECG data includes displaying said superimposition data for two channels of ECG data.

9. A system according to claim 7 wherein said superimposition template means further includes means for displaying an eight second strip of ECG data, said 8 second strip corresponding to said 8 second section of superimposition data.

10. A system according to claim 9 wherein said superimposition template means further includes bar graph display means for displaying bar graph data representing one minute of ECG data, said eight second strip of ECG data in said eight second strip display means and said eight second section of ECG data in said superimposition display means corresponding to at least a portion of said one minute section of ECG data in said bar graph display means.

11. A system according to claim 10 wherein said bar graph display means further includes a series of bars representing a series of heart beat waveforms, the positioning of each bar in said display corresponding to relative time intervals between each heart beat waveform.

12. A system according to claim 10 wherein said superimposition template means further includes a movable marker means positioned adjacent said bar graph display means for identifying an eight second section of said one minute of ECG data located in said bar graph display means, said eight second section of ECG data in said bar graph display means identified by said eight second marker means being related to said eight second section of ECG data in said eight second strip display means and said eight second section of superimposed ECG data in said superimpositioned display means.

13. A system according to claim 6 wherein said at least open template means includes a minute-by-minute ECG template means, said minute-by-minute ECG template means including an ECG display means for displaying a one minute section of ECG data, said minute-by-minute ECG template means further including beat morphology annotation data display means for indicating morphology of heart beart waveforms located in said one minute section of ECG data.

14. A system according to claim 13 wherein said minute-by-minute ECG template means further includes at least one operation box means for guiding interaction of a user with said system, said minute-by-minute ECG template means further including at least one data box means adjacent to and functionally related with said at least one operation box means for containing information related to said at least one operation box means.

15. A system according to claim 13 wherein said minute-by-minute ECG template means further includes means for highlighting beat rhythm patterns of the ECG data displayed in said ECG display means.

16. A system according to claim 15 wherein said highlighting means is capable of highlighting at least one beat rhythm pattern chosen from a plurality of beat rhythm patterns comprising: couplets, bigeminal bats, trigeminal beats, runs, superventricular tachycardia, dropped beats, and pauses.

17. A system according to claim 1 wherein said ECG data received by said playback means from said data storage medium includes a plurality of channels of analog ECG data and a plurality of channels of digital data related to analysis of said analog ECG data.

18. A system according to claim 1 further including recorder means operatively associated with said data storage medium for recording ECG data onto said data storage medium, said recorder means including means for recording at least a portion of said information in a reverse format, and said playback means including means for downloading said information recorded in said reverse format to said processor means.

19. An ambulatory ECG monitoring system comprising:
playback means for downloading ECG data from a cassette tape, said playback means including a microprocessor,
processor means for analysis, manipulation, and editing of data received from said playback means, and
playback/processor linking means for linking said playback means and said processor means for transfer of information between said playback means and said processor means,
said playback means further including a tape transport interface means, a speed control means and a clock track counter means, said tape transport interface means, said speed control means and said clock track counter means being operatively associated with each other and positioned in structurally cooperatively relationship with each other within said playback means,
whereby, said microprocessor can monitor the speed of said cassette tape in said tape transport interface means by counting clock track pulses on said cassette tape to define an actual tape speed and compare said actual tape speed to an expected tape speed defined by said clock track counter means, and send a corrected tape speed value to said speed control means, said speed control means adjusting a voltage input to said tape transport interface means to adjust the speed of said tape transport interface means.

20. A system according to claim 19 wherein said corrected tape speed value can adjust the speed of said tape transport interface means up to approximately plus or minus 10%.

21. A system according to claim 20 wherein said tape transport interface means further includes a low pass filter means for causing a gradual voltage change to occur in said tape transport interface means, whereby speed changes of said cassette tape are caused to occur gradually over a short period of time.

22. A real-time ECG analysis system for continuously recording ECG signals in analog format on a data storage medium, while simultaneously performing continuous real-time digital analysis of said ECG signals, said ECG analysis system including an ECG recorder for recording said ECG signals in analog format on said data storage medium said ECG recorder having a processor positioned therein which is operatively associated therewith for performing said continuous real-time digital analysis of said ECG signals simultaneously with aid recording of said ECG signals in analog format on said data storage medium, said ECG recorder further recording digital data on said data storage medium corresponding to said continuous real-time digital analysis performed by said processor.

23. A system according to claim 22 wherein said data storage medium is a tape.

* * * * *